US007790382B2

(12) United States Patent
Voces-Sanchez et al.

(10) Patent No.: US 7,790,382 B2
(45) Date of Patent: Sep. 7, 2010

(54) USE OF THE TRANSCRIPTION OF THE SLUG GENE IN EVALUATING THE REDISPOSITION OF A SUBJECT WITH CANCER TO DEVELOP METASTATIS

(75) Inventors: Felipe Voces-Sanchez, Salamanca (ES); Isidro Sanchez-Garcia, Salamanca (ES)

(73) Assignee: Oncostem Pharma, S.L., Salamanca (ES)

( * ) Notice: Subject to any disclaimer, the term of this patent is extended or adjusted under 35 U.S.C. 154(b) by 0 days.

(21) Appl. No.: 11/666,358

(22) PCT Filed: Oct. 25, 2005

(86) PCT No.: PCT/ES2005/000574

§ 371 (c)(1),
(2), (4) Date: Nov. 14, 2007

(87) PCT Pub. No.: WO2006/045874

PCT Pub. Date: May 4, 2006

(65) Prior Publication Data

US 2008/0108711 A1    May 8, 2008

(30) Foreign Application Priority Data

Oct. 25, 2004    (ES)    ............................... 200402559

(51) Int. Cl.
*C12Q 1/68*    (2006.01)
*C07H 21/04*    (2006.01)

(52) U.S. Cl. .......................................... 435/6; 536/23.1
(58) Field of Classification Search .................. None
See application file for complete search history.

(56) References Cited

U.S. PATENT DOCUMENTS

| 5,474,796 | A | * | 12/1995 | Brennan .................... 427/2.13 |
| 5,766,888 | A |   | 6/1998 | Sobol et al. |
| 2002/0004491 | A1 | * | 1/2002 | Xu et al. ........................ 514/44 |
| 2002/0119455 | A1 | * | 8/2002 | Chan ............................. 435/6 |
| 2006/0286570 | A1 | * | 12/2006 | Rowlen et al. ................. 435/6 |
| 2007/0009954 | A1 | * | 1/2007 | Wang et al. ..................... 435/6 |
| 2007/0031829 | A1 | * | 2/2007 | Yasuno et al. .................. 435/6 |
| 2007/0042400 | A1 | * | 2/2007 | Choi et al. ..................... 435/6 |
| 2007/0042419 | A1 | * | 2/2007 | Barany et al. .................. 435/6 |

FOREIGN PATENT DOCUMENTS

| EP | 1354962 |   | 10/2003 |
| EP | 1354962 | A1 * | 10/2003 |
| WO | WO-0102860 |   | 1/2001 |
| WO | WO 02/59361 | A * | 1/2002 |
| WO | WO-02059361 |   | 8/2002 |
| WO | WO-03046181 |   | 6/2003 |

OTHER PUBLICATIONS

Zhang et al., Bioinformatics, 2003, vol. 19, No. 1, pp. 14-21.*

Bolos et al. (2003). "The Transcription Factor Slug Represses E-cadherin Expression and Induces Epithelial to Mesenchymal Transitions: a Comparison with Snail and E47 Repressors," *J. Cell Sci.* 116(3):499-511.

Burchiel, S.W.I. & Rhodes, B.A., eds. (1982) *Tumor Imaging: The Radiochemical Detection of Cancer.* Masson Publishing Inc. (Table of Contents).

Chambers et al. (2000). "Proteomics: a new approach to the study of disease," *J. Pathol.* 192:280-288.

Choo et al. (1997). "Promoter-specific Activation of Gene Expression Directed by Bacteriophage-selected Zinc Fingers," *J. Mol. Biol.* 273:525-532.

Cobaleda et al. (2000). "In Vivo Inhibition by a Site-specific Catalytic RNA Subunit of RNase P Designed against the BCR-ABL Oncogenic Products: a Novel Approach for Cancer Treatment," *Blood* 95:731-737.

Conacci-Sorrell et al. (2003). "Autoregulation of E-cadherin Expression by Cadherin-cadherin Interactions: the Roles of Beta-cadherin Signaling, Slug, and MAPK," *J. Cell Biol.* 163(4):847-857.

Contesso, G. et al. (1989). "Tumor Grade as a Prognostic Factor in Primary Breast Cancer," *Eur. J. Clin. Oncol.* 25(3):403-409.

Dutrillaux et al. (1990). "Characterization of Chromosomal Anomalies in Human Breast Cancer," *Cancer Genet. Cytogenet.* 49:203-217.

Elloul et al. (2005). "Snail-, Slug- and Sip 1-E-cadherin ratio as Novel Parameters of Disease Aggressiveness in Metastatic Ovarian and Breast Carcinoma," Abstracts of the 10th International Congress of the Metastasis-Research-Society, Sep. 17-20, 2004. *Clinical & Experimental Metastasis* 21(7):650-651.

Garcia et al. (1995). "Tumorigenic activity of the BCR-ABL oncogenes is mediated by BCL2," *Proc. Natl. Acad. Sci.* USA 92:5287-5291.

Gebhart et al. (1986). "Cytogenic Studies on Human Breast Carcinomas." *Breast Cancer Res. Treat.* 8:125-138.

Hajra et al. (2002). "The SLUG Zinc-Finger Protein Represses E-cadherin in Breast Cancer," *Cancer Research* 62(6):1613-1618.

Hernandez et al. (1997). "Murine Hematopoetic Reconstitution after Tagging and Selection of Retrovirally Transduced Bone Marrow Cells," *Proc. Natl. Acad. Sci.* USA 94:13239-13244.

Huang, L., Hung, M-C., Wagner, E. (1999). *Nonviral Vectors for Gene Therapy.* Academic Press. (Table of Contents and Index).

Inukai et al. (1999). "SLUG, a Ces-1-related Zinc Finger Transcription Factor Gene with Antiapoptotic Activity, is a Downstream Target of the E2A-HLF Oncoprotein," *Molecular Cell* 4:343-352.

Jalkanen et al. (1985). "Heparan Sulfate Proteoglycans from Mouse Mammary Epithelial Cells: Localization on the Cell Surface with a Monoclonal Antibody," *J. Cell. Biol.* 101:976-985.

(Continued)

*Primary Examiner*—Bradley L Sisson
(74) *Attorney, Agent, or Firm*—Morrison & Foerster LLP

(57) ABSTRACT

The invention relates to the Slug gene, the replication, transcription or expression products thereof and products related with the regulation of said Slug gene or with the regulation, elimination or degradation of the expression or translation products of same, which can be used in the identification, prevention or treatment of the spread or development of metastasis in cancer patients, such as a patient suffering from a cancer with cancer cells that express the Slug gene.

5 Claims, 18 Drawing Sheets

OTHER PUBLICATIONS

Jalkanen et al. (1987). "Cell Surface Proteoglycan of Mouse Mammary Epithelial Cells Is Shed by Cleavage of Its Matrix-Binding Ectodomain from Its Membrane-Associated Domain," *J. Cell. Biol.* 105:3087-3096.

Jiang et al. (1998). "The Slug Gene is not Essential for Mesoderm or Neural Crest Development in Mice," *Developmental Biology* 198:227-285.

Kohler et al. (1975). "Continuous Cultures of Fused Cells Secreting Antibody of Predefined Specificity," *Nature* 256:495-497.

Losada et al. (2002). "Zinc-finger Transcription Factor Slug Contributes to the Function of the Stem Cell Factor C-kit Signaling Pathway," *Blood* 100(4):1274-1286.

Matsunaga et al. (2002). "Application of Differential Display to Identify Genes for Lung Cancer Detection in Peripheral Blood," *Int. J. Cancer* 10(5):592-599.

Nieto et al. (1994). "Control of Cell Behavior During Vertebrate Development by Slug, a Zinc Finger Gene," *Science* 264:835-849.

Pandey et al. (2000). "Proteomics to study genes and genomes", *Nature* 405:837-846.

Perez-Mancera et al. (2005). "SLUG in Cancer Development," *Oncogene* 24(19):3073-3082.

Schultze et al. (1996). "Efficient Control of Gene Expression by Single Step Integration of the Tetracycline System in Transgenic Mice," *Nature Biotechnology* 14:499-503.

Ward M.S. (1999). "The Use of Flow Cytometry in the Diagnosis and Monitoring of Malignant Hematological Disorders," *Pathology* 31:382-392.

International Search Report mailed on May 25, 2006, for PCT Application No. PCT/ES2005/000574 filed on Oct. 25, 2005, 3 pages.

* cited by examiner

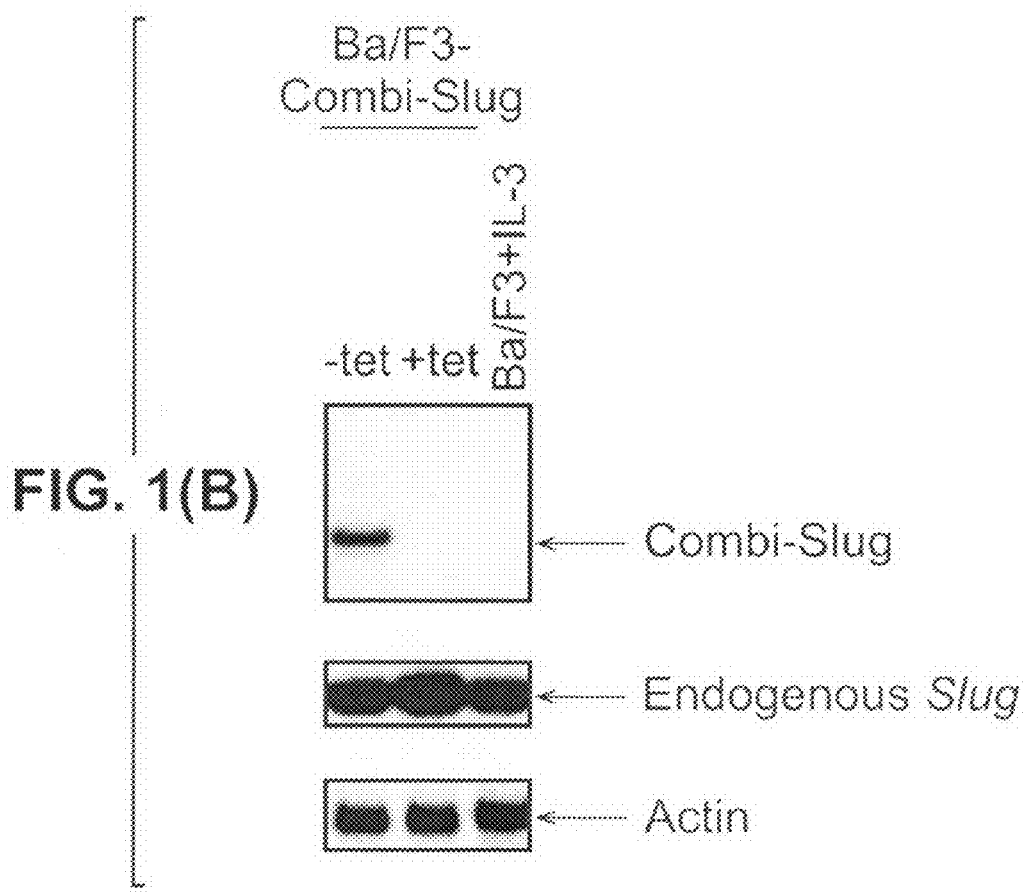

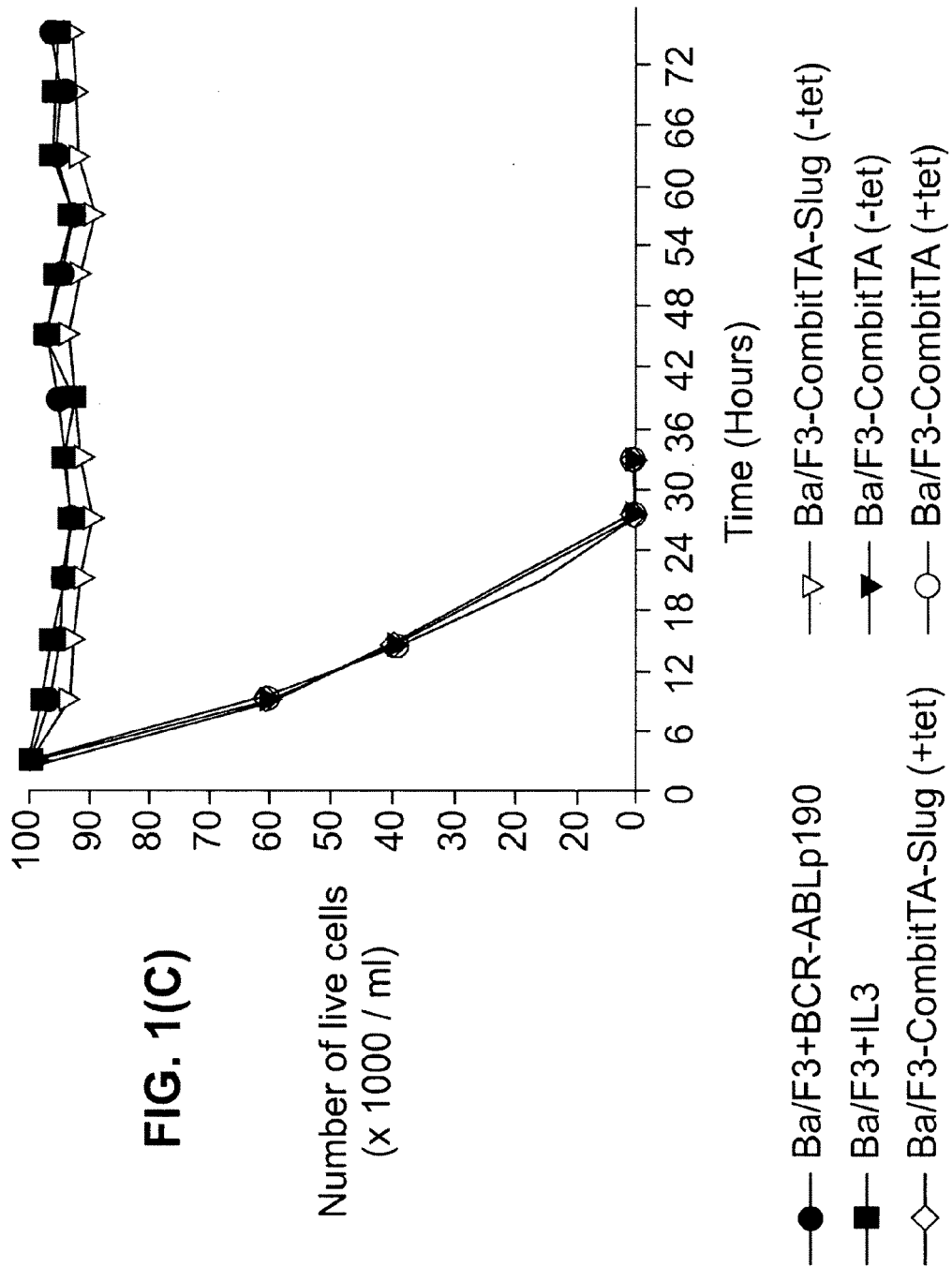

Solid Tumor

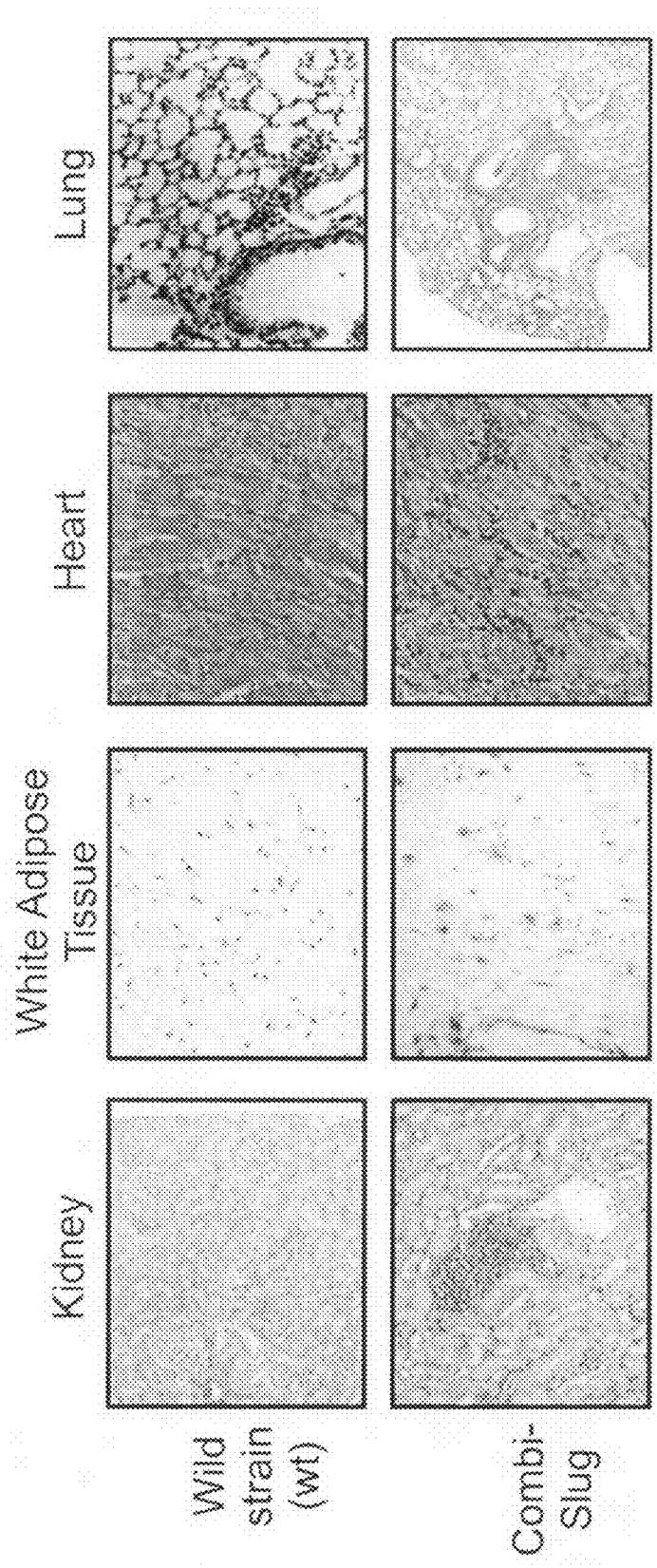

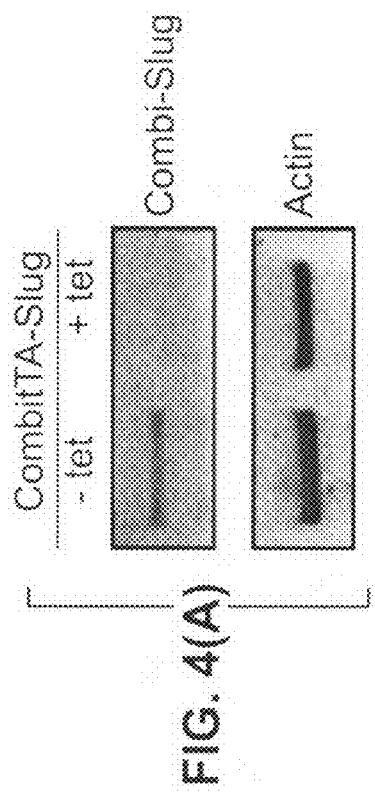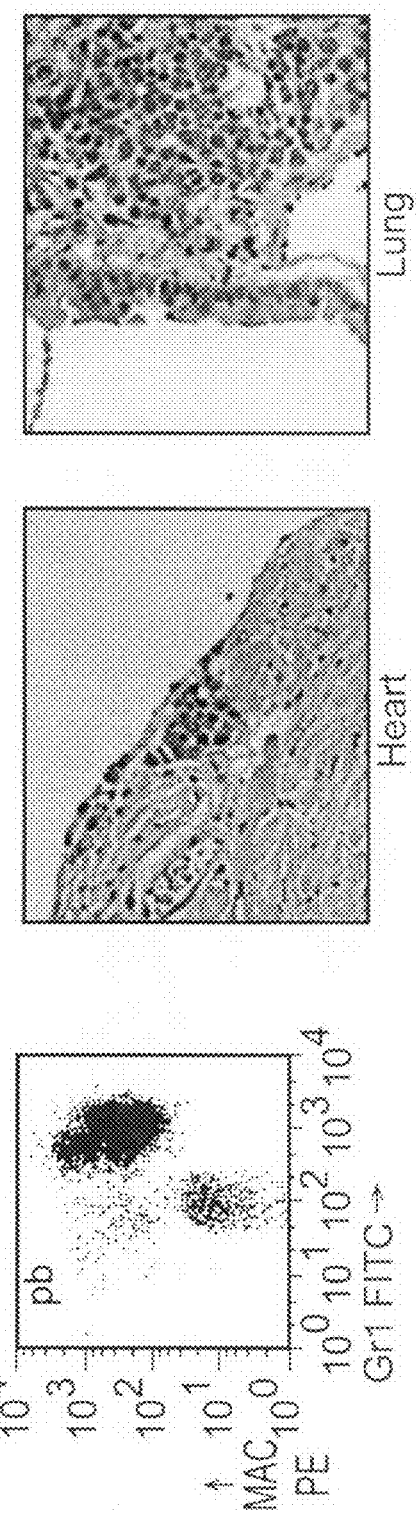
FIG. 4(A)
FIG. 4(B)

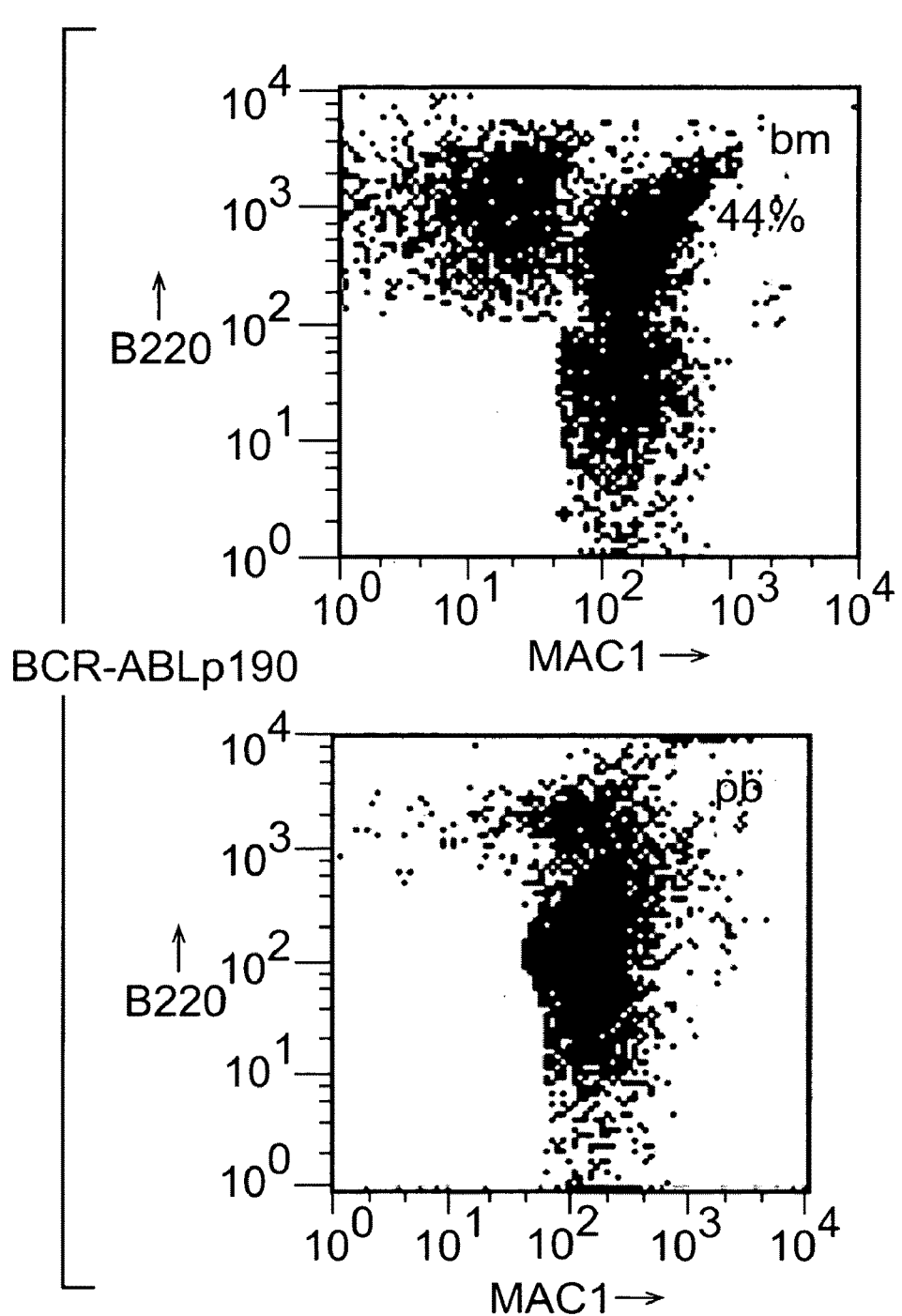
FIG. 6B(*II*)

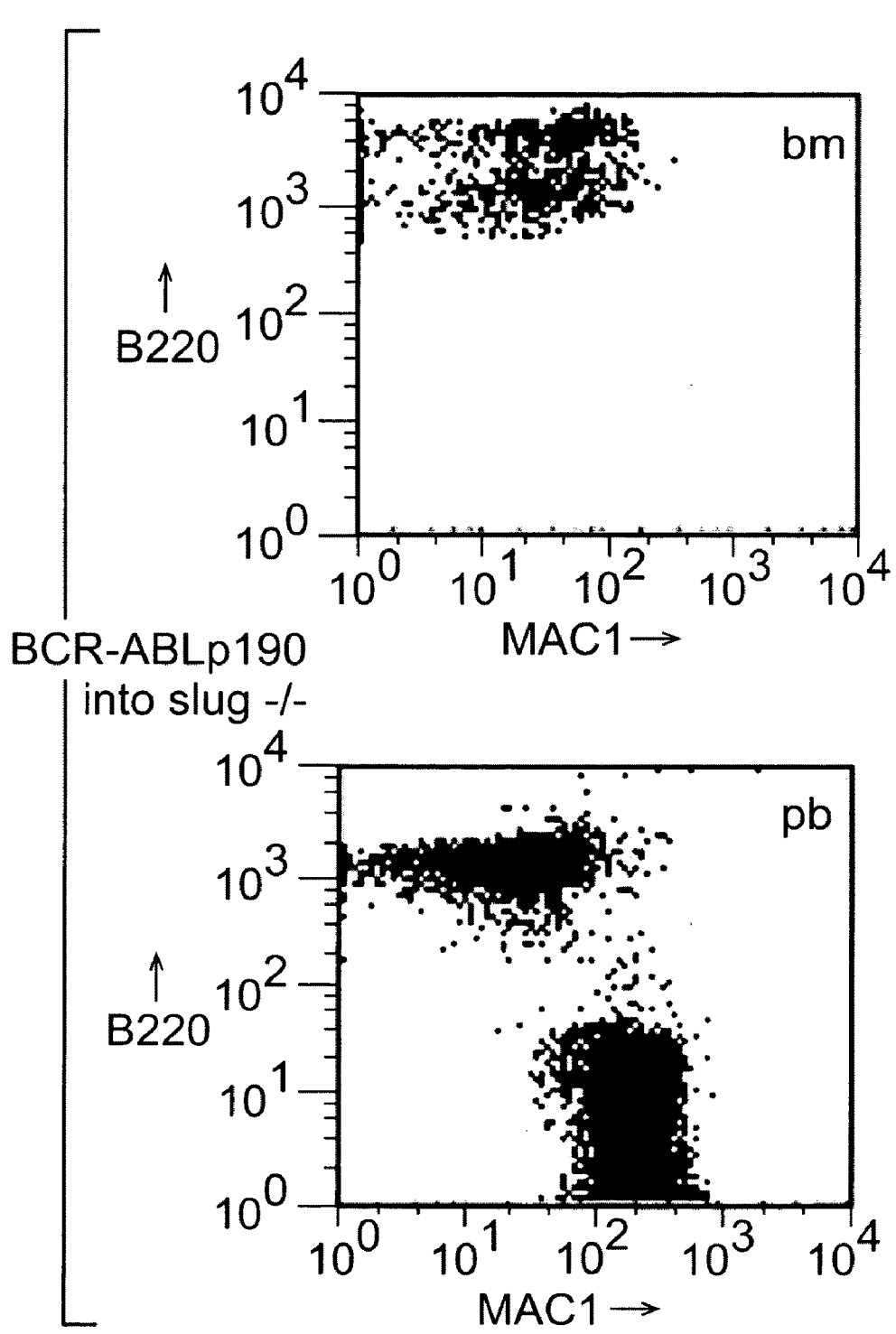

Probe: *Slug*

Probe: *Slug*

Probe: *Slug*

Probe: *Slug*

USE OF THE TRANSCRIPTION OF THE SLUG GENE IN EVALUATING THE REDISPOSITION OF A SUBJECT WITH CANCER TO DEVELOP METASTATIS

FIELD OF THE INVENTION

The invention relates to the use of the Slug gene and to its replication, transcription or expression products, as well as products associated with the regulation of said Slug gene or with the elimination or degradation of its products of expression or translation, in the identification, diagnosis, prevention or treatment of the spread or of the development of metastasis in cancer patients, such as a subject with a cancer whose cancerous cells express the Slug gene.

BACKGROUND OF THE INVENTION

Recent advances in cancer treatment have shown that in order to plan appropriate treatment of cancer and make an accurate prognosis it is necessary to have sensitive methods at one's disposal for detecting the presence of cancer, the type of cancer and its stage, for the purpose of determining its precise localization and its possible spread to other tissues. An accurate diagnosis of cancer can help to reduce the number of deaths from cancer and improve patients' quality of life, as it makes it possible to select the most appropriate treatment (chemotherapy, surgical resection, etc.) and reduce the patient's discomfort by defining the end point of therapeutic treatment.

Prognostic markers supply important information for the treatment and development of cancer in patients. In fact, for the application of systemic adjunctive therapy in the treatment of some types of primary cancers, identification of high-risk and low-risk patients is one of the main aims. Various prognostic markers are known, both classical markers, for example tumor size, state of the lymph nodes, histopathology, state of the steroid receptor, and second-generation markers, for example rate of proliferation, ploidy of the DNA, oncogenes, growth factor receptors and certain glycoproteins, which prove very useful for making therapeutic decisions (McGuire, W. L., Prognostic Factors for Recurrence and Survival, in "Educational Booklet American Society of Clinical Oncology", 25th Annual Meeting, 89-92 (1989); Contesso et al., Eur. J. Clin. Oncol., 25:403-409 (1989)). Although none of the known prognostic markers fully satisfies the aim of distinguishing between patients of low and high risk, by combining various markers it may be possible to improve the prediction of a patient's prognosis, therefore the search is continuing for new prognostic markers that could be added to those already available to assist in the prognosis of cancer, its progression and the residual disease after treatment. However, just as important as the prognosis of cancer is the diagnosis of possible metastasis in those patients who have already developed cancer, determining the degree of severity of the disease of a subject with cancer, or monitoring the effect of the treatment administered to a subject with cancer.

The genetic elements responsible for the invasion and metastasis of cancer are still unknown. It would therefore be helpful to identify diagnostic markers of invasiveness that could be analyzed in a simple manner.

SUMMARY OF THE INVENTION

It has now been found, surprisingly, that in various cancerous cells, both in mesenchymal and in carcinomatous tumor cells, there is expression of significantly raised levels of the Slug gene and/or its replication, transcription or translation products (gDNA, mRNA or protein), compared with normal cells, which offers an alternative to the current diagnostic methods, as it makes it possible to use the Slug gene and/or its associated products as a diagnostic marker of invasiveness (cancer spread and/or tumoral invasion) and as a therapeutic target for modulating said invasive activity of cancerous cells. Therefore, the expression or repression of the Slug gene and its replication, transcription or expression products, as well as products associated with the regulation of said Slug gene or with the elimination or degradation of its products of expression or translation, can be used for evaluating a cancer patient's risk of developing metastasis.

The expression or repression of the Slug gene and its replication, transcription or expression products, as well as products associated with the regulation of said Slug gene or with the elimination or degradation of its products of expression or translation, can be used for evaluating the predisposition of a subject with cancer, in particular a subject suffering from a cancer whose cancerous cells are Slug+ (i.e. whose cancerous cells express the Slug gene), to develop metastasis, or for evaluating the malignancy of a tumor, as well as for evaluating the degree of severity of the disease of a subject with cancer and/or for monitoring the effect of the treatment administered to a subject with cancer.

Therefore, one aspect of the invention relates to an in-vitro method (i) for evaluating the predisposition of a subject with cancer, such as a subject suffering from a cancer whose cancerous cells are Slug+, to develop metastasis, or (ii) for determining the degree of severity of the disease of said subject with cancer, or (iii) for monitoring the effect of the treatment administered to said subject with cancer, which comprises analyzing, in a sample of blood, or a derivative thereof, from said subject, at least one product of replication, transcription or translation of the Slug gene specific to the species of said subject and/or a product associated with the regulation of said Slug gene or with the regulation, elimination or degradation of its products of expression or translation.

Another aspect of the invention relates to an inhibitor of Slug or of its function, in the development of a pharmaceutical composition for treating, preventing or minimizing the development of metastasis in a subject with cancer, such as a subject suffering from a cancer whose cancerous cells are Slug+.

Further aspects will become clear to a person skilled in the art on reading the description.

BRIEF DESCRIPTION OF THE DRAWINGS

FIG. 1 shows the construction of the CombitTA-Slug transgene as well as the expression and effect of Slug in the survival of Ba/F3 cells devoid of growth factor. FIG. 1B shows the result of analysis of the tetracycline-dependent expression of Slug, by RT-PCR for CombitTA-Slug in Ba/F3 cells (−tet, +tet in the medium). The PCR products were transferred to a nylon membrane and were analyzed with a probe specific to Slug. Actin was used for ensuring the integrity of the DNA and the homogeneity of loading. FIG. 1C shows the results for survival of Ba/F3 cells that express Slug in the absence of IL-3. Cells that grew exponentially in medium supplemented with IL-3 amounted to $5 \times 10^5$ cells/ml on day 0, the IL-3 was withdrawn and they were cultivated. It shows the number of viable cells, of Ba/F3+p190 cells, of Ba/F3 cells grown in the presence of IL-3 and of Ba/F3 cells transfected with Slug grown in the absence of IL-3.

FIG. 3 reveals the presence of mesenchymal cancer in the CombitTA-Slug transgenic mice. FIG. 3C shows the histological appearance of various tissues of CombitTA-Slug mice; the cells that express Slug (Slug+ cells) disobey the social order of organ limits, migrate individually and produce metastasis in various regions.

FIG. 4 shows the phenotype of the CombitTA-Slug mice after suppression of Slug expression by treatment with tetracycline. FIG. 4A shows the result of analysis of the tetracycline-dependent expression of Slug in the blood of the transgenic CombitTA-Slug mice (−tet, +tet in water), by RT-PCR. Actin was used for ensuring the integrity of the DNA and the homogeneity of loading. FIG. 4B shows the phenotypic characteristics (according to investigation by flow cytometry) of the cells of the blood analyzed and tissue sections stained with hematoxylin/eosin of CombitTA-Slug mice after suppression of Slug expression by treatment with tetracycline (4 g/l) for 4 weeks.

FIG. 5 shows the expression of Slug in cells expressing BCR-ABL. Expression of human Slug (hSlug) and mouse Slug (mSlug) was analyzed by RT-PCR and the amplification products were transferred to a nylon membrane and were analyzed by hybridization with a specific probe. Actin or ABL was used for ensuring the integrity of the DNA and the homogeneity of loading.

FIG. 6 shows that Slug is necessary for the genesis of tumors in mice expressing BCR-ABL.

DETAILED DESCRIPTION OF THE INVENTION

Figure 1A:
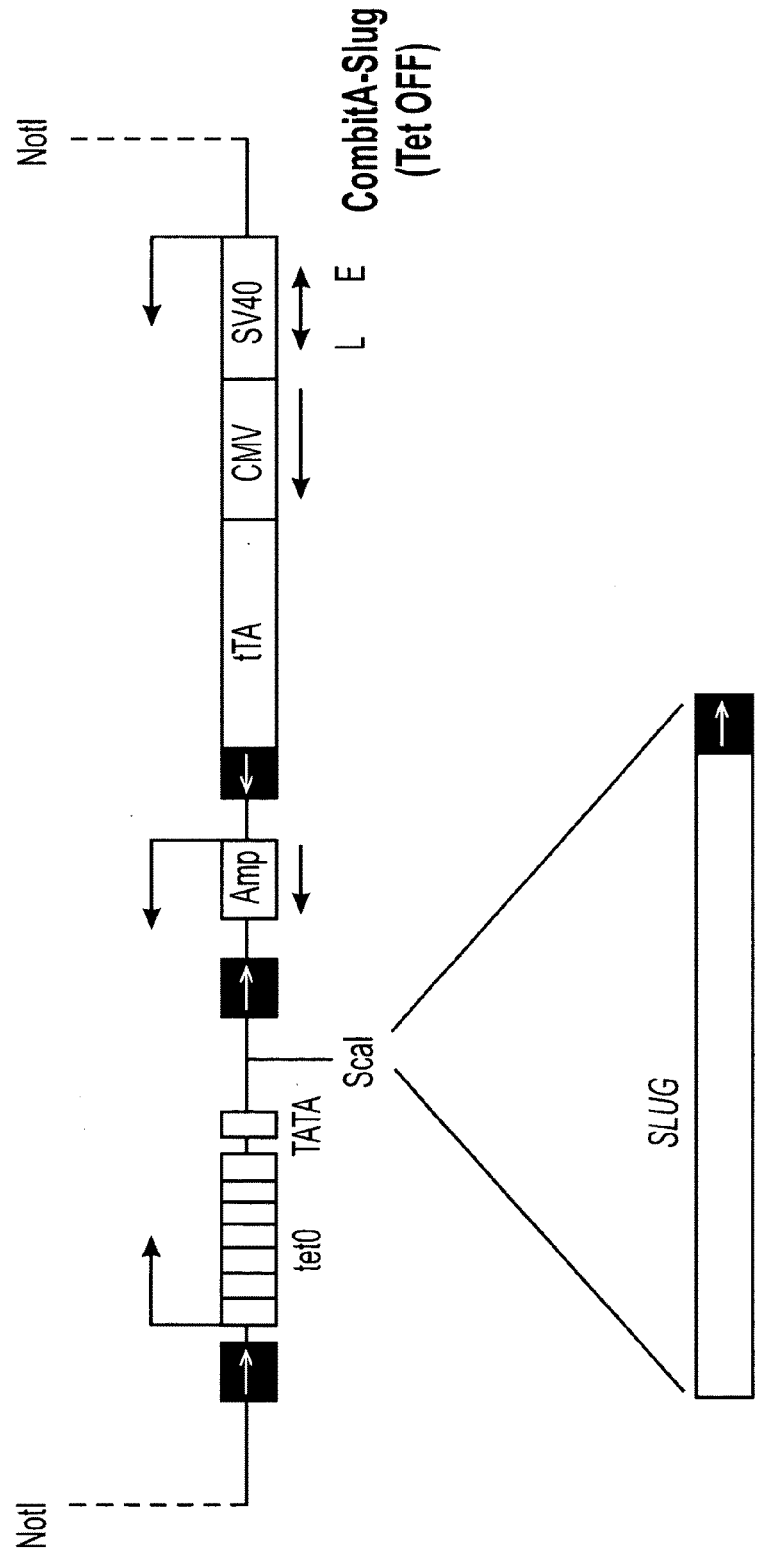
FIG. 1A is a schematic representation of the CombitTA-Slug vector.

The invention relates, in general, to the discovery that the expression of the Slug gene is connected with the spread of cancer and/or with tumoral invasion in a subject. Therefore, the expression or repression of the Slug gene and its replication, transcription or expression products, as well as products associated with the regulation of said Slug gene or with the elimination or degradation of its expression or translation products, can be used for evaluating the risk of a subject with cancer, such as a subject suffering from a cancer whose cancerous cells are Slug+, of developing metastasis, and consequently said gene and its replication, transcription and/or expression products, as well as products associated with the regulation of said Slug gene or with the elimination or degradation of its products of expression or translation, are markers of the malignancy of the cancer and constitute a very attractive target for treatment of the cancer.

The Slug gene is a gene present in vertebrates that codes for a transcription factor of the "zinc finger" type (Slug) involved in epithelial-mesenchymal transitions (Nieto et al., Science 264:835-849 (1994)). Use of the Slug gene, or its transcription or expression products, in the detection and/or treatment of cancerous cells has previously been described [WO 02/059361]. Use of the Slug gene and its expression product (Slug) has also been described in the mobilization of hematopoietic stem cells for transplant or gene therapy, in the ex vivo expansion of hematopoietic stem cells, and/or in the treatment of problems of male sterility [WO 03/046181].

It has now been discovered, surprisingly, that said Slug gene is not expressed in the blood of healthy individuals, but is indeed expressed in cancerous or tumoral cells. Apparently, the Slug gene inhibits the production of E-cadherin, preventing the cancerous cell adhering to the adjacent cells. In this process the malignant cell invades other tissues and organs, giving rise to metastasis, therefore the expression or repression of the Slug gene and its replication, transcription or expression products, as well as products associated with the regulation of said Slug gene or with the elimination or degradation of its products of expression or translation, can be used for evaluating the predisposition of a subject with cancer, such as a subject suffering from a cancer whose cancerous cells are Slug+, to develop metastasis, or for evaluating the malignancy of a tumor, as well as for evaluating the degree of severity of the disease of a subject with cancer and/or for monitoring the effect of the treatment administered to a subject with cancer.

Therefore, one aspect of the invention relates to an in-vitro method (i) for evaluating the predisposition of a subject with cancer, such as a subject suffering from a cancer whose cancerous cells are Slug+, to develop metastasis, or (ii) for determining the degree of severity of the disease of said subject with cancer, or (iii) for monitoring the effect of the treatment administered to said subject with cancer, hereinafter method of the invention, which comprises analyzing, in a sample of blood, or a derivative thereof, from said subject, at least one product of replication, transcription or translation of the Slug gene specific to the species of said subject and/or a product associated with the regulation of said Slug gene or with the regulation, elimination or degradation of its products of expression or translation.

As used in this description, the term "analyze" includes "measure and/or detect and/or identify and/or quantify".

Furthermore, the term "subject", as used, includes any vertebrate, such as a mammal, including human beings.

The method of the invention can be applied to any subject with cancer, i.e. a subject who is suffering from cancer or is suspected of suffering from cancer whose cancerous or tumoral cells express the Slug gene (Slug+ cancerous cells). Illustrative examples of cancerous cells that express the Slug gene include, among others, cells of mesenchymal or epithelial cancers, such as cells of leukemias and solid tumors, for example acute myeloid leukemias, leukemia cells with the t(17;19) translocation, lymphomas, sarcomas, for example rhabdomyosarcoma cells that express the PAX3-FKHR translocation, cells that express BCR-ABL, lung cancer, for example small-cell lung cancer, gynecological tumors, ovarian cancer, breast carcinomas, colon cancer, for example colonic tumors derived from Cajal interstitial cells (a type of SCF-dependent cell), etc. In a particular embodiment, said subject is a human being who is suffering from a mesenchymal or epithelial cancer, such as breast cancer, colon cancer, lung cancer, ovarian cancer, a sarcoma, a lymphoma, a leukemia or any other cancer whose cells are Slug+.

The presence, in a sample of blood, or a derivative thereof, obtained from a subject with cancer, of replication, transcription or translation products of the Slug gene specific to the species of said subject and/or of products associated with the regulation of said Slug gene or with the elimination or degradation of its products of expression or translation, is indicative of a predisposition of said subject with cancer to develop metastasis. Moreover, the presence and amount of said products may be indicative of the degree of severity of the disease of said subject with cancer and/or of the effect of the treatment administered to said subject with cancer for the purpose of evaluating the efficacy of the treatment administered to the subject and, if it is ineffective, carrying out modification of the therapeutic regimen to be applied to the subject and monitoring its efficacy.

The method of the invention can be carried out using a sample of blood, or a derivative thereof, from a subject to be analyzed, that contains at least one product of replication, transcription or translation of the Slug gene specific to the species of said subject and/or a product associated with the regulation of said Slug gene or with the elimination or degradation of its products of expression or translation. The term "blood" as used here includes whole blood or a fraction thereof. The blood is taken from the subject by conventional methods. Blood derivatives include plasma, serum, cellular fraction, etc., which can be obtained by conventional methods known to a person skilled in the art. The blood is taken from the subject by conventional methods.

In a particular embodiment, the method of the invention comprises the analysis, in said sample of blood, or a derivative thereof, from a subject with cancer, such as a subject with a cancer whose cells are Slug+, of a product of replication of the Slug gene specific to the species of said subject, such as, for example, genomic DNA (gDNA) of said Slug gene or a fragment thereof.

In another particular embodiment, the method of the invention comprises the analysis, in said sample of blood, or a derivative thereof, from a subject with cancer, such as a subject with a cancer whose cells are Slug+, of a product of transcription of the Slug gene specific to the species of said subject, such as, for example, messenger RNA (mRNA) of the Slug gene, a fragment of said mRNA, complementary DNA (cDNA) to the RNA that codes for the product of transcription or expression of said Slug gene, a fragment of said cDNA, or mixtures thereof.

The analysis of said products of replication or transcription of the Slug gene, indicative of the expression or repression of said gene, can be carried out by means of any suitable test for detecting, identifying and/or quantifying nucleic acids. In general, said tests are based on reactions of mapping, sequencing, hybridization, amplification, etc. and visualization of the reaction products by any suitable technique, both radioactive and non-radioactive, for example by techniques of colorimetry, fluorometry, luminescence (for example bioluminescence, chemiluminescence, etc.), etc. Examples illustrating said tests include sequencing, mapping with S1 nuclease, polymerase chain reaction (PCR), reverse transcription in combination with the polymerase chain reaction (RT-PCR), quantitative PCR, real-time PCR, hybridization, Southern blot, Northern blot, RNA Protection Assay, etc. As an illustration, the analysis of said products of replication or transcription of the Slug gene is carried out by means of an assay that comprises enzymatic amplification of the whole or a fragment of said product of replication or transcription of the Slug gene, for example by RT-PCR, and hybridization with a probe specific to Slug, optionally labeled with a suitable marker, for example radioactive nucleotides, haptens, enzymes, etc.

In a particular embodiment, the expression (or repression) of the Slug gene can be evaluated by determining the level of mRNA corresponding to the Slug gene, or by determining the number of copies of the Slug gene produced. In the sense employed in this description, "determination of the level of mRNA" includes any method that makes it possible to measure or estimate, qualitatively or quantitatively, the level of mRNA that can be translated into the Slug protein in the cells of a test sample by either directly or relatively comparing it with the level of Slug mRNA in the cells of a control sample. Moreover, "determination of the number of copies of Slug gene produced" includes any method that makes it possible to measure or estimate qualitatively or quantitatively the number of copies of the Slug gene produced in cells of a test sample by either directly or relatively comparing it with the number of copies of the Slug gene produced in cells of a control sample. Determination of the number of copies of the Slug gene can be carried out by any suitable conventional method, for example by visualizing extrachromosomal double fragments [extrachromosomal double minutes (dmin)] or integrated homogeneously staining regions (hsrs) (Gebhart et al., Breast Cancer Res. Treat. 8:125 (1986); Dutrillaux et al., Cancer Genet. Cytogenet. 49:203 (1990)), by hybridization techniques using suitable probes obtained by conventional methods in view of the nucleotide sequence of the Slug gene, etc. In addition, the level of Slug mRNA can be determined by other suitable conventional methods, for example by analysis by Northern blot, mapping with S1 nuclease, PCR, RT-PCR, techniques of hybridization, arrays, etc.

In another particular embodiment, the method of the invention comprises the analysis, in said sample of blood, or a derivative thereof, from a subject with cancer, such as a subject with a cancer whose cells are Slug+, of a product of translation of the Slug gene specific to the species of said subject, for example the Slug protein or a fragment thereof.

Analysis of said product of translation of the Slug gene can be carried out by means of any suitable test for detecting, identifying and/or quantifying proteins, for example by techniques based on the use of antibodies, flow cytometry, proteomics, etc. As an illustration, the expression of the Slug protein can be analyzed by a Western blot or dot-slot assay (Jalkanen et al., J. Cell. Biol. 101:976-985 (1985); Jalkanen et al., J. Cell. Biol. 105:3087-3096 (1987)), or by means of immunoassays based on the formation of complexes by cross reactions, of the antigen-antibody type, in which the specific recognition is provided by an antibody to the Slug protein or to a fragment thereof, for example an antigenic fragment thereof, and visualization of the complexes formed by any suitable technique, both radioactive and non-radioactive, for example by techniques of colorimetry, fluorometry, luminescence (for example bioluminescence, chemiluminescence, etc.), etc., using for it, as appropriate, secondary antibodies labeled with suitable markers; examples of said immunoassays include ELISA (enzyme-linked immunosorbent assay), RIA (radioimmunoassay), immunohistochemical, immunofluorescent and immunoprecipitation assays, etc. The antibodies to be used are antibodies to the Slug protein or to a fragment thereof, for example an antigenic fragment of the Slug protein, optionally conjugated with a carrier. The antibodies can be polyclonal or, preferably, monoclonal, which can be obtained by conventional methods, for example using hybridoma technology (Kohler et al., Nature 256:495 (1975)). Alternatively it is possible to use fragments of antibodies, for example Fab, $F(ab')_2$, etc.

Other methods for determining Slug expression include flow cytometry (Ward M. S., Pathology 31:382-392 (1999), proteomics (Pandey M. & Mann M., Nature 405:837-846 (2000); Chambers et al., J. Pathol. 192:280-288 (2000), etc.

In a particular embodiment, analysis of said product of translation of the Slug gene is carried out by means of an assay that comprises the use of an antibody, for example a polyclonal antibody or, preferably, a monoclonal antibody, specific to the Slug protein or to a fragment thereof, that recognizes an epitope of said protein or fragment, and visualization of the complex formed by conventional methods.

In addition, expression of the product of translation of the Slug gene can be detected in vivo using imaging diagnostic techniques in vivo based on the use of anti-Slug antibodies bound to suitable markers, for example markers detectable by X-rays, nuclear magnetic resonance (NMR), etc. A review of tumor diagnosis by imaging is given in Tumor Imaging: The Radiochemical Detection of Cancer (S. W. Burchiel & B. A. Rhodes, eds., Masson Publishing Inc. (1982)).

In another particular embodiment, the method of the invention comprises the analysis, in said sample of blood, or a derivative thereof, from a subject with cancer, such as a subject with a cancer whose cells are Slug+, of a product associated with the regulation of the Slug gene specific to the species of said subject. As used here, the expression "product associated with the regulation of the Slug gene" relates to any product involved directly or indirectly in the regulation of the Slug gene, both at the nucleic acid level and at the protein level. In a particular embodiment, said product associated with the regulation of the Slug gene is a transcription factor that is involved in the regulation of said gene. Illustrative examples of said product associated with the regulation of the Slug gene include the stem cell factor (SCF), the c-kit cytokine, etc.

In another particular embodiment, the method of the invention comprises the analysis, in said sample of blood, or a derivative thereof, from a subject with cancer, such as a subject with a cancer whose cells are Slug+, of a product associated with the regulation, elimination or degradation of the products of expression or translation of the Slug gene specific to the species of said subject. As used here, the expression "product associated with the elimination or degradation of its products of expression or translation of the Slug gene" relates to any product involved directly or indirectly in the regulation, elimination or degradation of the products of expression or translation of the Slug gene, both at the nucleic acid level and the protein level. In a particular embodiment, said product associated with the regulation, elimination or degradation of the products of expression or translation of the Slug gene is a protein or an antibody that directly or indirectly causes the regulation, elimination or degradation of the products of expression or translation of the Slug gene, both at the nucleic acid level and at the protein level.

Said products associated with the regulation of the Slug gene as well as said products associated with the regulation, elimination or degradation of the products of expression or translation of the Slug gene, depending on their nature (nucleotide or peptide), can be analyzed by conventional methods.

In a particular embodiment, when said products associated with the regulation of the Slug gene or said products associated with the regulation, elimination or degradation of the products of expression or translation of the Slug gene are of a nucleotide nature, said products can be analyzed by any suitable test for detecting, identifying and/or quantifying nucleic acids, such as those mentioned previously in connection with said products of replication or transcription of the Slug gene but using the appropriate reagents (initiators, probes, etc.).

Moreover, in another particular embodiment, when said products associated with the regulation of the Slug gene or said products associated with the regulation, elimination or degradation of the products of expression or translation of the Slug gene are of a peptide or protein nature, said products can be analyzed by any suitable test for detecting, identifying and/or quantifying proteins, such as those mentioned previously in connection with said products of translation of the Slug gene.

As mentioned previously, the presence of replication, transcription or translation products of the Slug gene specific to the species of said subject and/or of products associated with the regulation of said Slug gene or with the regulation, elimination or degradation of its products of expression or translation, in a sample of blood, or a derivative thereof, obtained from a subject with cancer, such as a subject with a cancer whose cells are Slug+, is indicative of a predisposition of said subject with cancer to the spread of the cancer and/or to develop metastasis, or of the degree of severity of the disease of said subject with cancer or of the effect of the treatment administered to said subject with cancer for the purpose of assessing the efficacy of the treatment applied to said subject.

Therefore, the repression, total or partial, of the expression of the Slug gene or of the activity of the Slug protein could be useful for treating, preventing or minimizing the risk or predisposition of a subject with cancer to develop metastasis.

Accordingly, the invention further relates to the reduction, inhibition or repression of the Slug gene, its products of replication, transcription or translation, for treating, preventing or minimizing the development of metastasis in a subject with cancer, such as a subject with a cancer whose cells are Slug+. The reduction, inhibition or repression of the Slug gene, its products of replication, transcription or translation, can be achieved by the use of inhibitors of Slug or of its function. The Slug gene, its products of replication, transcription or translation, as well as said products associated with the regulation of the Slug gene or with the regulation, elimination or degradation of the products of expression or translation of the Slug gene can be used in the search for inhibitors of Slug or of its function, which can be used in the treatment or prevention of the development of metastasis in subjects with cancer.

Therefore, another aspect of the invention relates to the use of an inhibitor of Slug or of its function, in the development of a pharmaceutical composition for treating, preventing or minimizing the development of metastasis in a subject with cancer, such as a subject with a cancer whose cells are Slug+.

As used in this description, the term "inhibitor of Slug or of its function" includes any compound that interferes with, reduces, cancels or suppresses the expression of the Slug gene as well as any compound able to interfere with the function of the Slug protein or of the Slug gene, or which inhibits or reduces the effects regulated by the Slug gene and its products of replication, transcription or translation, for example a compound with the capacity to interfere with Slug at the nucleic acid level (gDNA, cDNA, RNA) or protein level (Slug). The effects regulated by the Slug gene and its products of replication, transcription or translation include cellular migration, for example in epithelial-mesenchymal transitions, the development and survival of lines of melanocytes and hematopoietic lines, the migration and/or survival of Leydig cells, mobilization of hematopoietic stem cells, resistance to damage in the DNA, cellular resistance to irradiation, etc. The effects regulated by the Slug gene and/or its products of replication, transcription or translation might be inhibited or reduced by various mechanisms, for example by inhibiting the endogenous production of Slug. Illustrative examples of compounds that are potentially useful as inhibitors of Slug include non-functional transcription factors of the "zinc finger" type.

In general, interference with the function of the Slug gene can be effected at DNA level by preventing its expression, inactivating the mRNA that is generated by means of antisense oligonucleotides or ribozymes, inactivating the protein by the use of antibodies or having the effect of said protein compete with dominant negatives [Choo Y. et al. J. Mol. Biol., 1997, 273:525-532; Cobaleda C. and Sánchez-García I. Blood, 2000, 95:731-737] and/or, in general, by using any compound that represses the expression of the Slug gene or represses or inhibits the formation or the activity of its products of transcription or translation. As an illustration, said inhibitor of Slug or of its function can be a protein, a peptide, a transcription factor of the non-functional "zinc finger" type, an antisense oligonucleotide, a ribozyme, an antibody or an antibody fragment.

In a particular embodiment, said inhibitor of Slug is an antisense oligonucleotide, i.e. a compound which, when administered to a cell that expresses the Slug gene, for example a tumoral cell that expresses the Slug protein, is able for example to reduce, cancel, or repress the expression of the Slug gene, thus reducing the levels of the Slug protein or eliminating them completely, or to repress or inhibit the formation or the activity of the products of transcription or translation of the Slug gene. Said antisense oligonucleotide might bind specifically, for example, to the mRNA of the Slug gene, thereby preventing its translation to the Slug protein. Information on gDNA, cDNA or mRNA of the Slug gene and/or of the Slug protein, in particular of the human Slug gene (hSlug) or of the human Slug protein (hSlug) can be found in WO 02/059361 as well as in the literature references contained in said document; in addition, information on the mouse Slug gene (mSlug) or the mouse Slug protein (mSlug) can be found in Nieto et al. (Nieto et al., Science 264:835-849 (1994)). Said antisense oligonucleotide comprises a suitable nucleotide sequence and a suitable length for hybridization with the nucleotide sequence of the Slug gene or its product of replication or transcription, under highly stringent conditions. By way of illustration, said antisense oligonucleotide comprises at least 8 consecutive nucleotides, preferably at least 12, 16 or 20 consecutive nucleotides of the nucleotide sequence of the Slug gene or capable of hybridizing with the nucleotide sequence of the Slug gene under highly stringent conditions, such as, for example, SSPE 5× and 0.5% SDS, at 65° C. or equivalent conditions. Examples of antisense oligonucleotides that can be used for preventing expression of the Slug gene can be found in WO 02/059361.

In another particular embodiment, said inhibitor of Slug or of its function is an anti-Slug antibody, such as an antibody that recognizes the intact Slug protein or a fragment thereof, such as an antigenic fragment thereof, optionally conjugated to a carrier. The anti-Slug antibodies can be polyclonal or, preferably, monoclonal, which can be obtained by conventional methods, for example by means of hybridoma technology. Alternatively, it is possible to use fragments of antibodies, for example Fab, F(ab')$_2$, etc., which can be obtained by conventional methods, which recognize the Slug protein or an antigenic fragment thereof.

The pharmaceutical composition provided by this invention comprises at least one inhibitor of Slug or of its function, in a therapeutically effective amount, and a pharmaceutically acceptable excipient. Said pharmaceutical composition can contain one or more inhibitors of Slug or of its function, i.e. one or more compounds capable of reducing, cancelling or repressing the expression of the Slug gene, so it is useful for preventing or treating the development of metastasis in subjects with cancer, in particular in subjects suffering from cancers whose cancerous cells are Slug+. Illustrative examples of tumorous cells or cancerous Slug+ cells include, among others, cells of mesenchymal or epithelial cancers, such as cells of leukemias and solid tumors, for example acute myeloid leukemias, leukemia cells with the t(17;19) translocation, lymphomas, sarcomas, for example rhabdomyosarcoma cells that express the PAX3-FKHR translocation, cells that express BCR-ABL, lung cancer, for example small-cell lung cancer, gynecological tumors, ovarian cancer, breast carcinomas, colon cancer, for example colonic tumors derived from Cajal interstitial cells (a type of SCF-dependent cell), etc.

Therefore, said inhibitor of Slug or of its function could be used, moreover, in the treatment, as adjunctive or principal therapy, of said tumors and cancers.

The excipients that can be used in the production of the pharmaceutical composition supplied by this invention will depend, among other things, on the ways of administering said pharmaceutical composition. A review of the various ways of administering active principles, of the excipients to be used and of the methods of manufacture thereof can be found in the Tratado de Farmacia Galénica [Treatise of Galenical Pharmacy], C. Faulí and Trillo, Luzán 5, S. A. de Ediciones, 1993.

In a particular embodiment, the pharmaceutical composition supplied by this invention is a composition intended for administration by the intravenous route (i.v.) or intraperitoneal route (i.p.). In another particular embodiment, the pharmaceutical composition supplied by this invention is a composition intended for use in gene therapy that comprises a viral or non-viral vector, and an inhibitor of Slug or of its function. By way of illustration, said vectors can be viral vectors, for example based on retroviruses, adenoviruses, etc., or non-viral vectors such as DNA-liposome, DNA-polymer, DNA-polymer-liposome complexes, etc. [see "Nonviral Vectors for Gene Therapy", edited by Huang, Hung and Wagner, Academic Press (1999)].

The following examples illustrate the invention and should not be regarded as limiting it in any way.

Example 1

Development of Cancer by Deregulation of Slug Expression

I. Materials and Methods

Cell cultures The cell lines used include the Ba/F3 hematopoietic precursor cell line [Palacios and Steinmetz, Cell 41:727 (1985)] and Ba/F3 cells that express the human proteins BCR-ABL$^{p190}$ (Ba/F3+p190) and BCR-ABL$^{p210}$ (Ba/F3+p210) [Sánchez-García and Grütz, Proc. Natl. Acad. Sci. USA, 92:5287-5291 (1995)]. The cells were kept in Dulbecco's modified Eagle's medium (DMEM) supplemented with 10% fetal bovine serum (FBS). 10% of medium conditioned with WEHI-3B as a source of IL-3 (interleukin-3) was added when necessary.

Cellular transfection and Survival test The Ba/F3 cells were transfected by electroporation (960 μF, 220 V) with 20 μg of CombitTA-Slug plasmid. The population of neomycin-resistant cells (Ba/F3+CombitTA-Slug) was analyzed by RT-PCR (reverse transcription-polymerase chain reaction) for detecting expression of CombitTA-Slug in the presence and absence of tetracycline (20 ng/ml). These cells were resistant to the withdrawal of IL-3 when grown in the absence of tetracycline. Resistance of the cells to IL-3 withdrawal was confirmed, and cellular viability was determined by exclusion of trypan blue.

RT-PCR To analyze expression of CombitTA-Slug and of endogenous Slug in mouse cell lines and in mice, RT-PCR was carried out following the manufacturer's instructions in a reaction volume of 20 μl containing 50 ng of random hexamers, 3 μg of total RNA and 200 units of reverse transcriptase Superscript II RNase H⁻ (GIBCO/BRL). 30 cycles were carried out at 94° C. for 1 minute, 56° C. for 1 minute and 72° C. for 2 minutes, using the sequences of the specific primers stated below:

```
                                   (SEQ ID NO: 1)
Combi-polyA-B1:    5'-TTGAGTGCATTCTAGTTGTG-3';

(SEQ ID NO: 2)
forward mSlug:     5'-GTTTCAGTGCAATTTATGCAA-3';

(SEQ ID NO: 3)
reverse mSlug:     5'-TTATACATACTATTTGGTTG-3'.
```

Amplification of the RNA of β-actin served as control for guaranteeing the quality of the RNA samples.

In addition, for analyzing the expression of hSlug in human cell lines and in blood samples from Ph$^1$-positive patients, the parameters of the cycles used in the PCR reactions, and the sequences of the specific primers were as follows:

hSlug: 30 cycles at 94° C. for 1 minute, 56° C. for 1 minute and 72° C. for 2 minutes, forward primer 5'-GCCTC-CAAAAAGCCAAACTA-3' (SEQ ID NO: 4) and reverse primer 5'-CACAGTGATGGGGCTGTATG-3' (SEQ ID NO: 5);

c-ABL: 30 cycles at 94° C. for 1 minute, 56° C. for 1 minute and 72° C. for 2 minutes, forward primer 5'-GTATCATCT-GACTTTGAGCC-3' (SEQ ID NO: 6) and reverse primer 5'-GTACCAGGAGTGTTTCTCCA-3' (SEQ ID NO: 7).

Amplification of the mRNA of c-ABL served as quality control of the samples.

Analysis by Southern blot DNA obtained from fragments of the tails of the mice was digested with restriction endonucleases as described previously [García Hernández et al., (1997). *Proc. Natl. Acad. Sci. U.S.A.*, 94, 13239-13244], separated by 0.8% agarose gel electrophoresis and transferred to a Hybond-N filter (Amersham). The DNA was fixed to the filters by exposure to ultraviolet radiation. The filters were hybridized with a cDNA probe from the complete sequence of Slug, corresponding to the complete cDNA of Slug [Pérez Losada et al., (2002). Blood, 100(4):1274-1286], labeled radioactively with $^{32}$P [García Hernández et al., (1997), cited above].

Generation of Transgenic Mice

CombitTA-Slug mice. The mouse Slug cDNA (mSlug) [Nieto et al., Science 264:835-849 (1994)] was cloned in the Combi-tTA vector [Schultze et al. (1996) Nature Biotechnology, 14: 499-503]. The assembly was cut to make it linear by digestion with NotI, and was injected into fertilized ova of CBAxC57B/J6 mice [Jackson Laboratory]. The transgenic mice were identified by Southern analysis of the DNA from a small fragment of the tail, after digestion with EcoRI. The cDNA of mSlug was used for detection of the transgene.

Mice with the Slug$^{\Delta 1}$ mutation Mice that are homo- and heterozygotic for the Slug$^{\Delta 1}$ mutation, generated by suppression of the complete gene sequence coding for the Slug protein (Slug$^{\Delta 1}$ mutant mice or mice lacking Slug) have been described previously [Jiang et al., (1998). Developmental Biology. 198; 277-2855].

Heterozygotic Slug +/− mice (Slug$^{\Delta 1}$ mice) were crossed with CombitTA-Slug transgenic mice and BCR-ABL$^{p190}$ transgenic mice (EP 1354962) to produce composite heterozygotic mice. The animals of the first generation (F1) were crossed to obtain mice without Slug (Slug −/−), heterozygotic for Combi-tTA and BCR-ABL$^{p190}$.

Histological analysis The animals included in this study were submitted to standard necropsy. All the major organs were examined under a dissection microscope, samples from each of them were embedded in paraffin, sections were prepared and were examined histologically. All the samples were obtained from viable, homogeneous parts of the dissected tissue and were fixed in the next 2-5 minutes. Then, tissue samples, stained with hematoxylin and eosin, were reexamined. Mice of the same age were used for the comparative studies.

Phenotypic analysis The following monoclonal antibodies were used for flow cytometry: CD45R/B220, IgM, Mac1, Gr-1 (Pharmingen). Single-cell suspensions obtained from different tissue samples obtained by routine techniques were incubated with a purified antibody against mouse CD32/CD16 to block binding to the Fc receptors, and with a suitable dilution of the various antibodies, at room temperature or at 4° C., respectively. The samples were washed twice with phosphate-buffered saline (PBS) solution and were resuspended in PBS. The dead cells in the samples were excluded by staining with propidium iodide. The samples and the data were analyzed with a FACScan flow cytometer and with the CellQuest computer program (Becton Dickinson).

Analysis of low molecular weight DNA The low molecular weight DNA was isolated as described below. The cells were collected in 1.5 ml of culture medium, they were centrifuged for 1 minute at 1500 rpm (400×g), and the pellet was resuspended in 300 µl of proteinase K buffer. After incubation overnight at 55° C., the DNA was precipitated with ethanol, resuspended in 200 µl of TE buffer (Tris-EDTA (ethylenediamine tetraacetic acid)) containing 50 µg/ml of RNAase A and incubated at 37° C. for 2 hours. The DNA was extracted with phenol/chloroform and was precipitated with ethanol. DNA aliquots (2 µg) were labeled terminally with $\alpha^{32}$P-dCTP and were submitted to 2% agarose gel electrophoresis. After electrophoresis, the DNA in the gel was transferred to a Hybond-N membrane (Amersham) and was submitted to autoradiography for 2 hours at −70° C.

Test of tumor-forming capacity To investigate the tumor-forming capacity of various cancers, $10^6$ cells suspended in 200 µl of PBS were injected subcutaneously into both flanks of athymic (nude) male mice. The animals and the growth of the tumors were monitored for 3 weeks.

II. Results

Figure 1D:
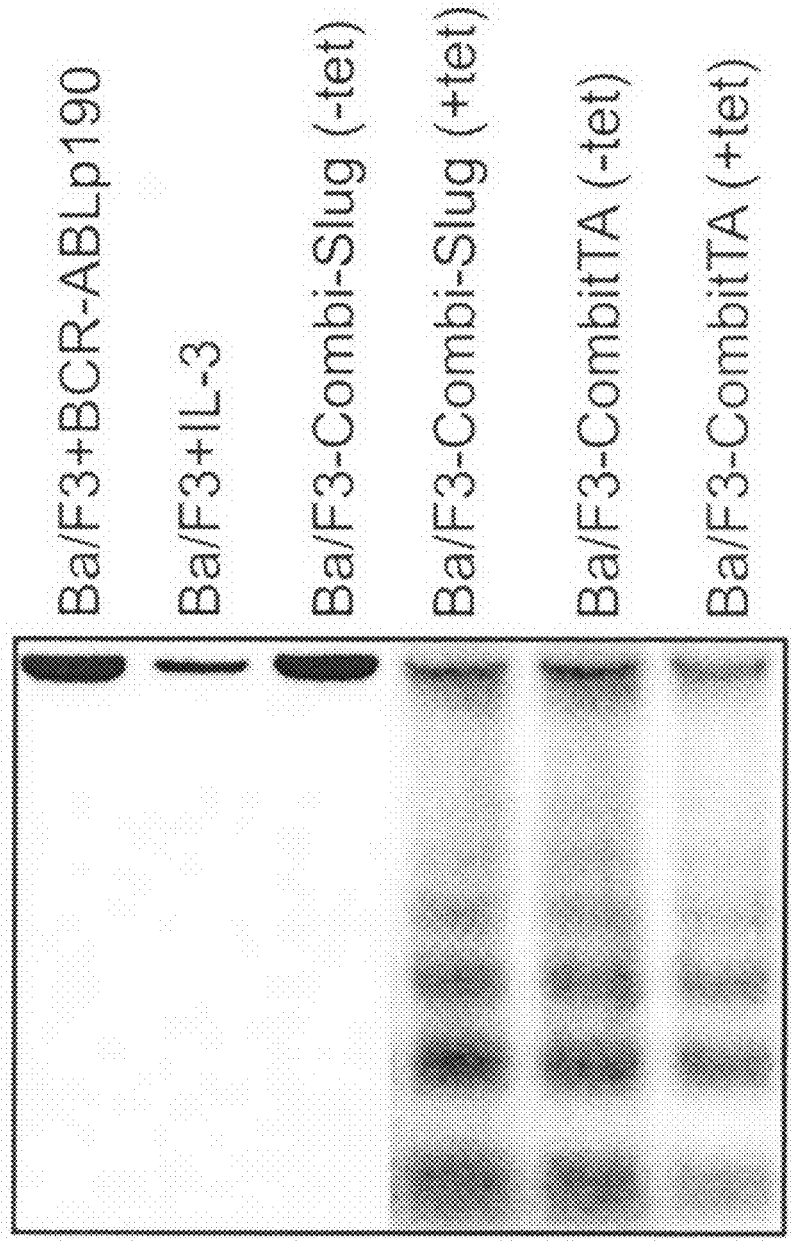
FIG. 1D demonstrates that cell death is accompanied by nucleosome ladders after withdrawal of IL-3. Twenty-four hours after withdrawal of IL-3, DNA of low molecular weight was isolated, which originated from Ba/F3+ BCR-ABL$^{p190}$ cells (lane 1), Ba/F3 cells grown in the presence of IL-3 (lane 2), Ba/F3-Combi-Slug cells grown in the absence of IL-3 and doxycycline (−tet) (lane 3), and Ba/F3-Combi-Slug cells grown in the absence of IL-3 and in the presence of doxycycline (+tet) (lane 4). The DNA was labeled terminally with α$^{32}$P-dCTP, was resolved by 2% agarose gel electrophoresis and was visualized by autoradiography.

Production of the CombitTA-Slug mice To determine whether deregulation of Slug expression is necessary for the development of cancer, some transgenic (CombitTA-Slug) mice were produced in which expression of the Slug gene could be regulated exogenously. For this we used the Combi-tTA system, which has, in a single plasmid, the transactivator and the tet-operator (tetO) minimum promoter for directing gene expression. This method ensures integration of the same number of copies of the transactivator as of the reporter gene in forward cis configuration, at the same point of the same chromosome, and prevents genetic segregation of the control elements during crossing. Insertion of the mSlug gene under the control of the tetO minimum promoter produces the CombitTA-Slug plasmid (FIG. 1A), which was tested in the Ba/F3 hematopoietic precursor cell line. The tet repressor protein, fused to the viral transactivation domain of VP16 (within tTA) binds, in the absence of tetracycline, to a genetically engineered tet minimum promoter and activates the transcription of CombitTA-Slug. In the presence of the effector molecule, this gene is not expressed and the promoter is silenced (FIG. 1B). After culture for two days, both in the presence and in the absence of tetracycline, expression of CombitTA-Slug was measured. In this way, the presence of CombitTA-Slug was detected in Ba/F3 cells in the absence, but not in the presence, of tetracycline (20 ng/ml). These data indicate that tetracycline completely represses the induction of CombitTA-Slug. The fact that expression of Slug protects Ba/F3 cells from apoptosis induced by withdrawal of IL-3 has already been demonstrated [Inukai et al. (1999). Molecular Cell. 4:343-352]. Next therefore we investigated the survival of Ba/F3 cells that expressed CombitTA-Slug, 24 hours after withdrawal of IL-3. Expression of Slug was sufficient for all the Ba/F3 cells expressing CombitTA-Slug to resist death induced by withdrawal of IL-3. Treatment with tetracycline restored the sensitivity of the Ba/F3 cells to withdrawal of IL-3 (FIGS. 1C and 1D).

Figure 2A:
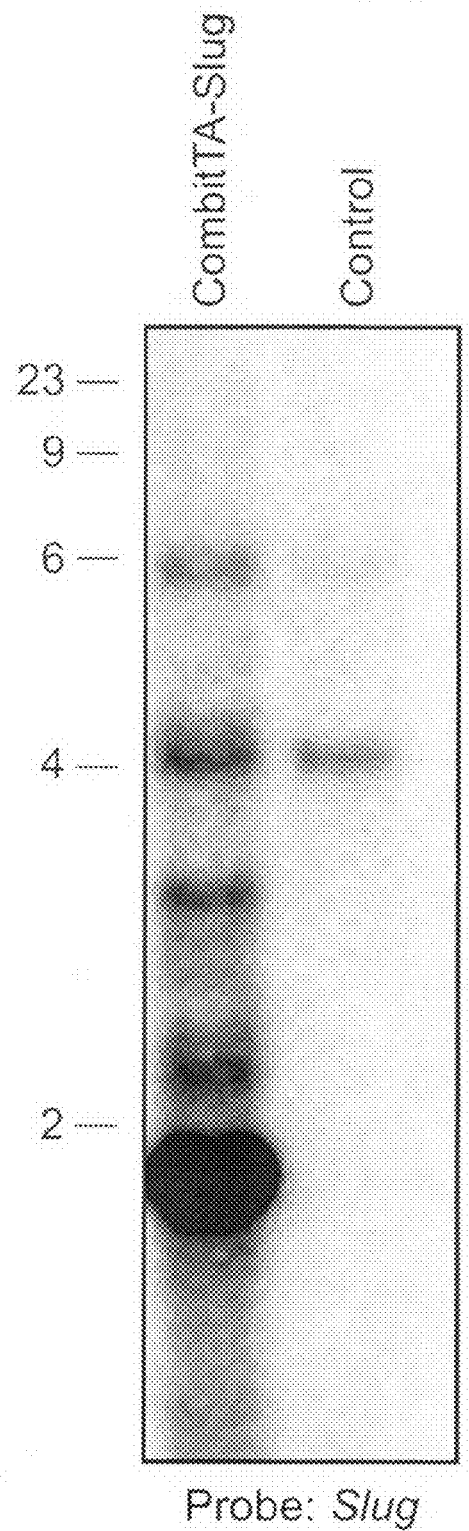
FIG. 2A shows identification of the transgenic mice by Southern blotting of the DNA from a small fragment from the tail after digestion with EcoRI, and mouse Slug cDNA was used for detection of the transgene. Expression of the transgene was demonstrated by RT-PCR (FIG. 2B); the expression of CombitTA-Slug and of endogenous Slug was analyzed by RT-PCR of tissue samples obtained from CombitTA-Slug and control mice. The PCR products were transferred to a nylon membrane and were analyzed by hybridization with a specific probe. Actin was used for ensuring the integrity of the DNA and the homogeneity of loading.
Figure 2B:
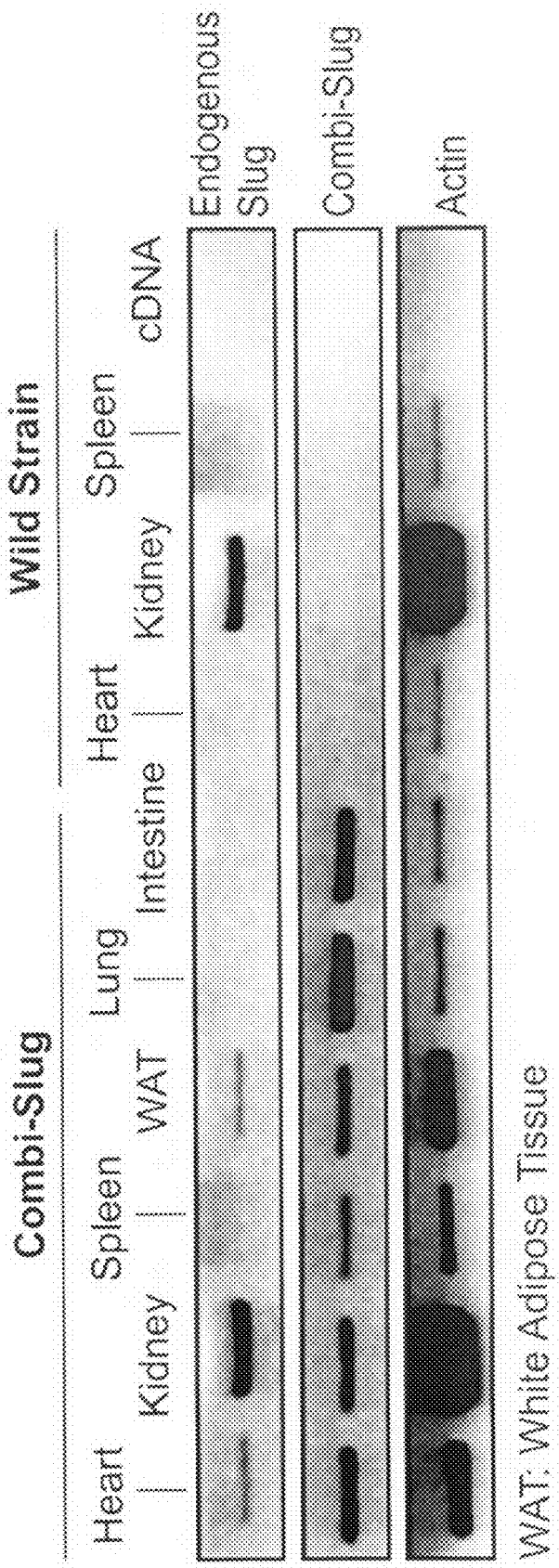
FIG. 2 shows the expression of the transgene in CombitTA-Slug transgenic mice.
FIG. 2C shows the results of analysis of the tetracycline-dependent expression of Slug, by RT-PCR for CombitTA-Slug, of samples of bone marrow from Slug −/− mice (−tet, +tet in the medium).
Figure 2C:
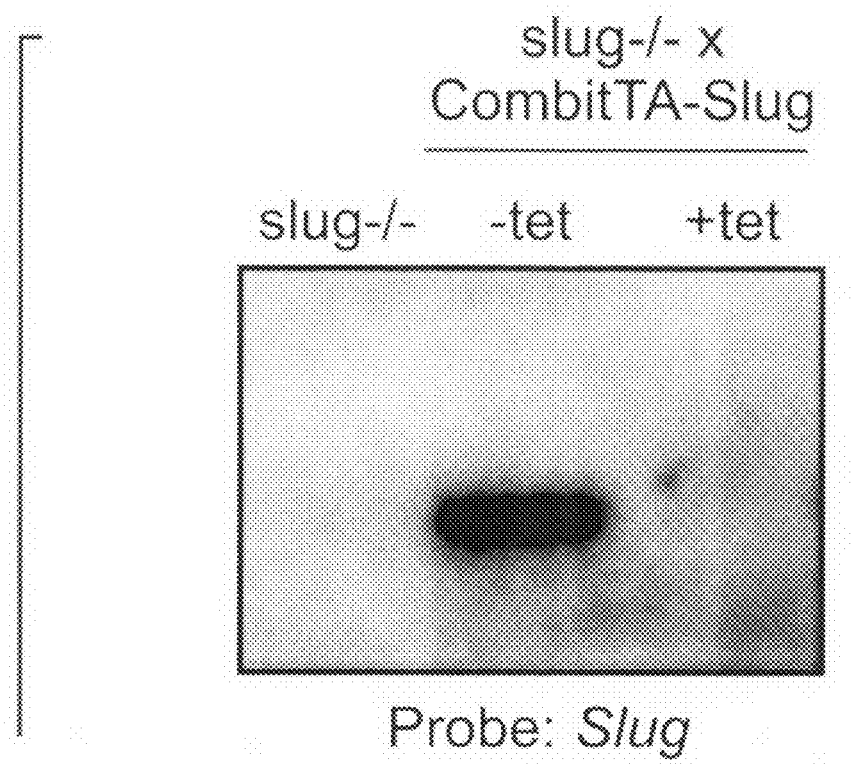
Figure 2C:
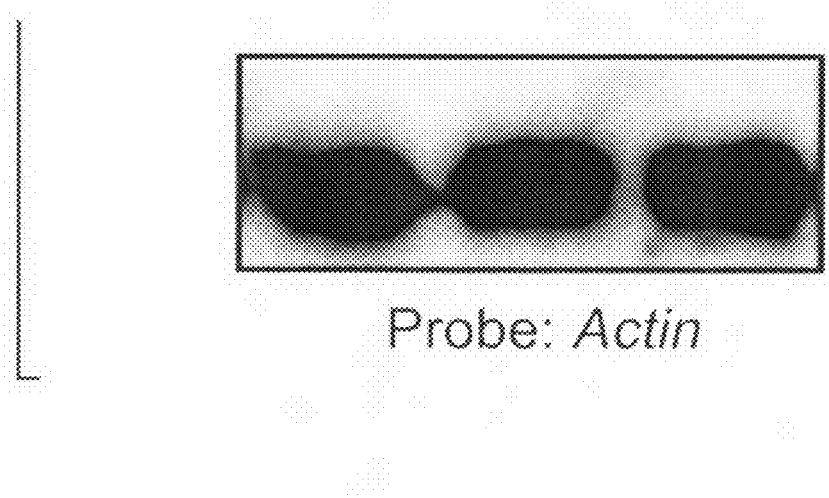

Two transgenic lines of CombitTA-Slug mice were created (FIG. 2A). In both, expression of CombitTA-SLUG could be detected reproducibly in all the tissues analyzed (FIG. 2B). The physiological importance of said CombitTA-Slug mice was analyzed by crossing with mice lacking Slug (Slug$^{\Delta 1}$ mutant mice). Anemia and the pigmentation defects characteristic of the homozygotic mice with mutant Slug did not occur in mice of this type crossed with CombitTA-Slug transgenic mice. Expression of CombitTA-Slug took place by transactivation, since in the mice that were administered tetracycline (4 mg/mL) in water, transactivation fell to undetectable levels (FIG. 2C).

Figure 3A:
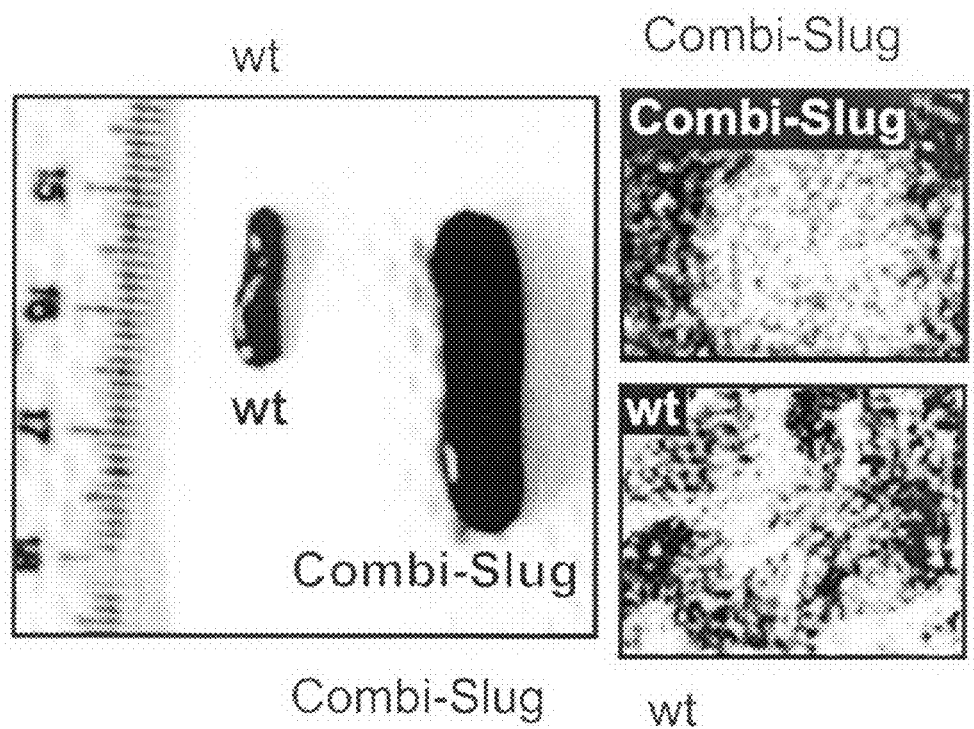
FIG. 3A shows the macroscopic appearance of tissue sections stained with hematoxylin/eosin from the spleen of mice from the wild-type strain and CombitTA-Slug. The spleen of the CombitTA-Slug mice shows change in the normal splenic architecture.
Figure 3B:
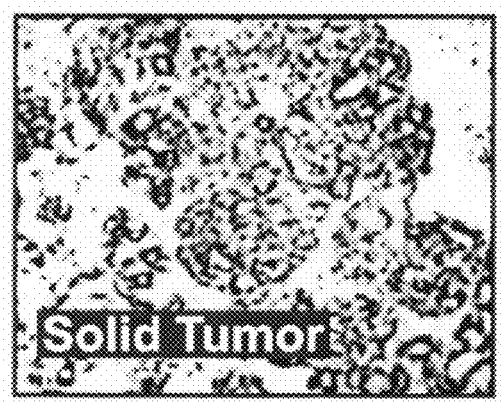
FIG. 3B shows the histological appearance of a solid tumor in CombitTA-Slug mice, after staining with hematoxylin/eosin.
Figure 3D:
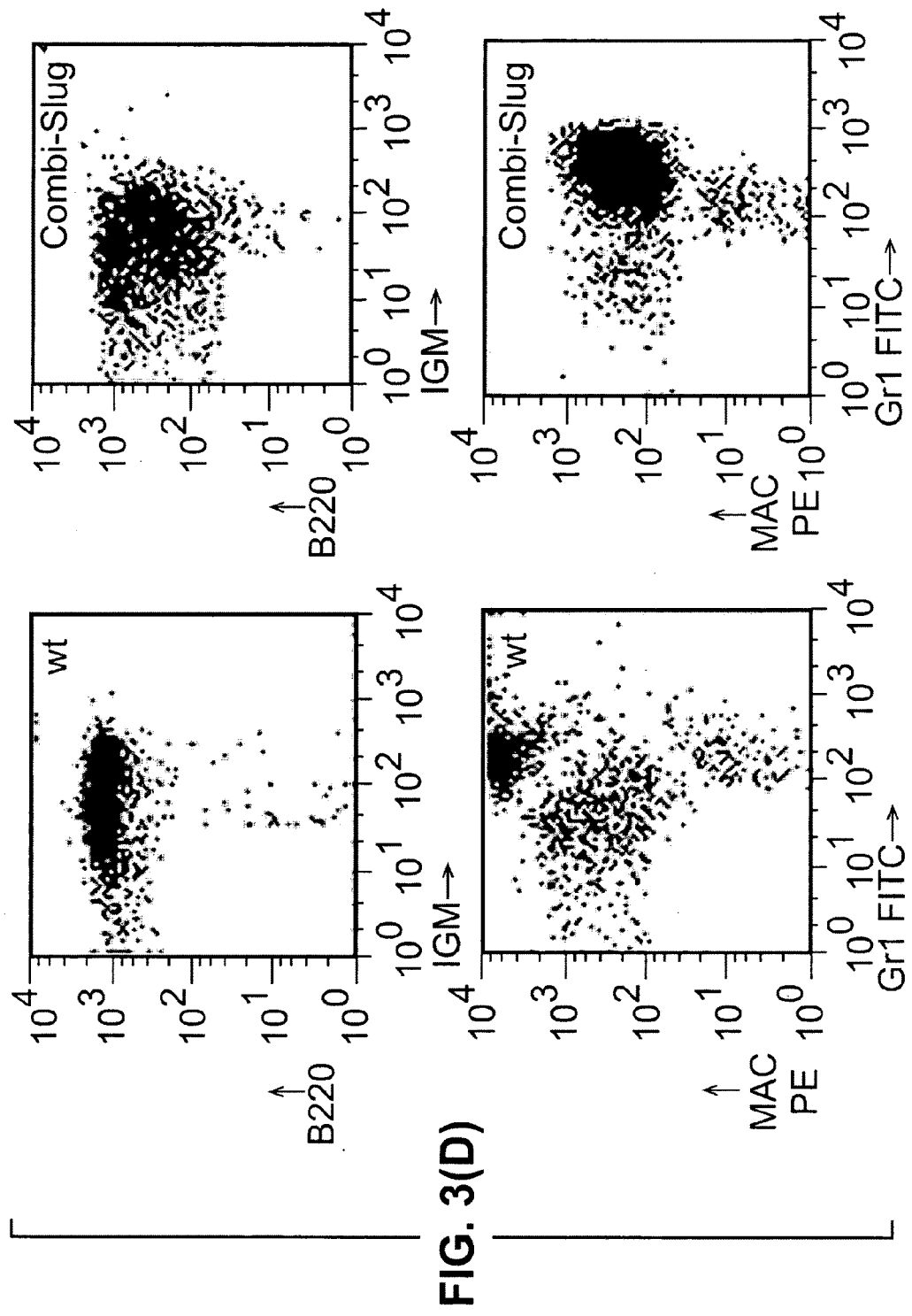
FIG. 3D shows the phenotypic characteristics of the leukemias of the CombitTA-Slug mice; the blood cells of the CombitTA-Slug mice were analyzed by flow cytometry; the different cells were identified with specific combinations of antibodies; 10,000 cells were analyzed from each sample, and dead cells were excluded by analysis after staining with propidium iodide.

Development of cancer in CombitTA-Slug transgenic mice. In humans, Slug is linked to mesenchymal cancerous cells that express fusion genes as a result of chromosomal abnormalities (leukemias or sarcomas). For this reason, we investigated whether the CombitTA-Slug transgenic mice developed mesenchymal cancers, and it was observed that all the CombitTA-Slug transgenic mice showed clear signs of failing health starting from 9 months of age. The clinical picture of these mice worsened rapidly, with development of mesenchymal cancers (90% developed leukemia and 10% sarcomas) (FIGS. 3A and 3B), which were characterized clinically by a decrease in mobility in the cage, increased breathing rate, piloerection, trembling and substantial weight loss. This condition persisted and the animals were sacrificed. Macroscopic examination showed splenomegaly (FIG. 3A) or sarcomas (FIG. 3B). Generally, the thymus glands were normal. These observations are consistent with mesenchymal cancers. However, neither epithelial changes nor carcinomas were observed in any of the 77 CombitTA-Slug mice analyzed despite extensive expression of CombitTA-SLUG. Histological examination of these animals revealed marked leukemic filtration of the hematopoietic and non-hematopoietic tissues (FIG. 3C). The mononuclear cells of the blood from the leukemic mice analyzed permitted diagnosis of the leukemias generated as B-cell acute lymphoblastic leukemia or acute myeloid leukemia (FIG. 3D).

The cells transplanted subcutaneously in healthy mice obtained from CombitTA-Slug transgenic mice developed the same type of tumor, as can be deduced from the histological examination. Moreover, it was verified that the cells forming the tumor originated from the donor by PCR, which revealed the presence of the CombitTA-Slug product. These data make it possible to define the tumors that developed in CombitTA-Slug transgenic mice as malignant, demonstrate that Slug causes mesenchymal cancer and indicate that Slug does not require prior formation of a tumor for spread to occur.

Irreversibility of the changes induced by Slug The above results provide evidence that expression of Slug endows the cells with the ability to migrate. Accordingly, Slug (nucleic acid or expression product) might become an attractive therapeutic target for controlling the invasive capacity of human cancers. If that is so, it might be hoped that cells that overexpress Slug would display changes in the patterns of growth and spread on modifying their level of expression of Slug. Therefore, the consequences of suppression of Slug were evaluated by means of phenotypic examination of 10 CombitTA-Slug transgenic mice, in which the presence of leukemia had previously been confirmed by analysis of their blood prior to treatment with tetracycline. Administration of tetracycline (4 g/l) in water to the CombitTA-Slug transgenic mice for 2 weeks caused suppression of Slug expression (FIG. 4A). However, no phenotypic modification was observed in any of the 10 CombitTA-Slug mice analyzed, despite suppression of Slug expression following treatment with tetracycline. Flow cytometry analysis of the animals treated with tetracycline revealed persistence of leukemic cells in the blood (FIG. 4B), and histological examination confirmed infiltration of the non-hematopoietic tissues (FIG. 4B).

Figure 5A:
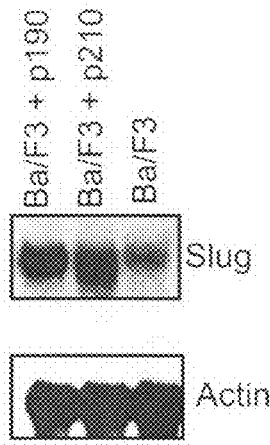
FIG. 5A shows the result of analysis of expression of Slug in Ba/F3 cells expressing BCR-ABL, both Ba/F3+p190 (lane 1) and Ba/F3+p210 (lane 2), and in Ba/F3 cells (lane 3).
Figure 5B:
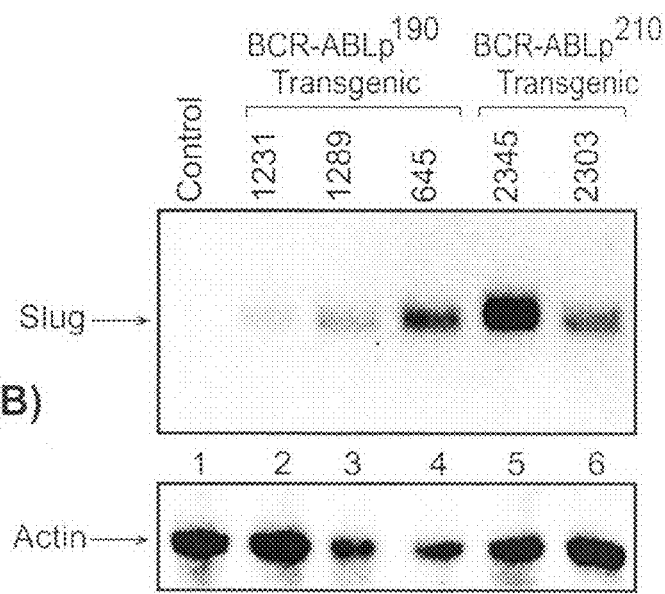
FIG. 5B shows the results of the expression of Slug in blood from BCR-ABL$^{p190}$ and BCR-ABL$^{p210}$ transgenic mice; the results were collected from the blood of the control mice (lane 1) and BCR-ABL$^{p190}$ (lanes 2 to 4) and BCR-ABL$^{p210}$ (lanes 5 and 6) transgenic mice.
Figure 5C:
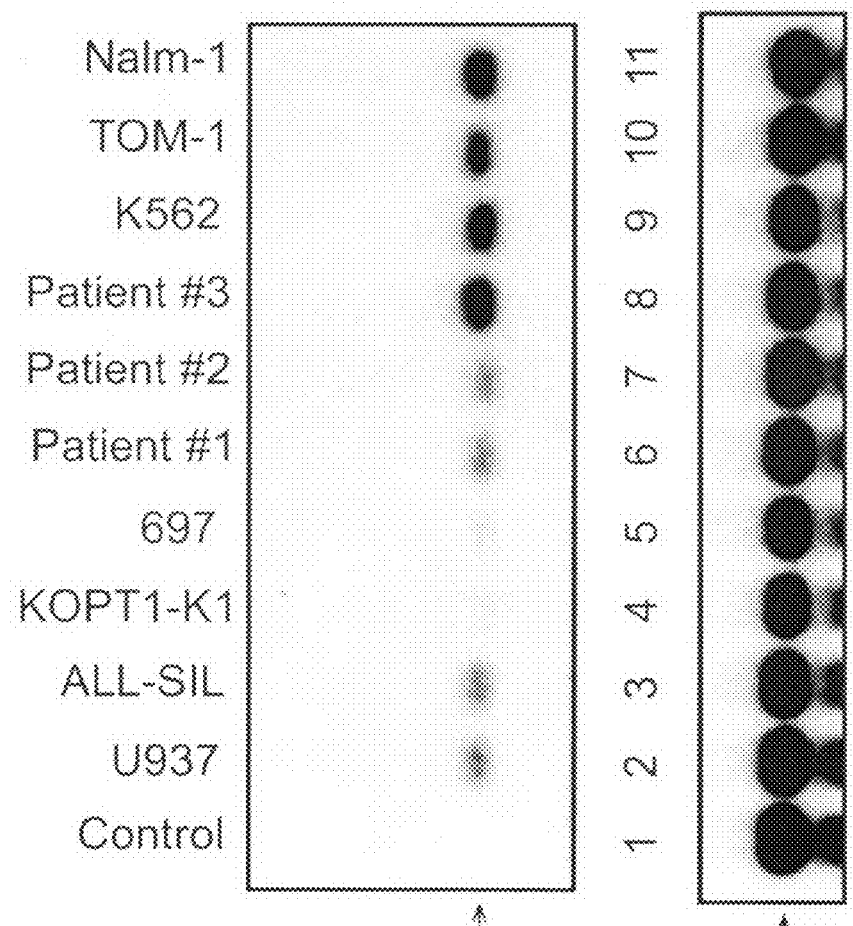
FIG. 5C reveals that Slug is present in human leukemia cell lines and in samples from patients with t(9;22): control human blood (lane 1), the myeloid leukemia cell line U937 (lane 2), the leukemia lines T ALL-SIL (lane 3) and KOPTI-KI (lane 4), the pre-B 697 leukemia cell line (lane 5), blood from patients with t(9;22) (lanes 6 to 8; patients 1 and 3 presented Ph-B-ALL, and patient 2 a myeloblastic crisis), and the leukemia cell lines t(9;22)-positive K562 (lane 9), TOM-1 (lane 10) and Nalm-1 (lane 11).

Suppression of Slug blocks in vivo the development of BCR-ABL$^{190}$ leukemia A critical step for understanding the malignant transformation mediated by oncogenes associated with mesenchymal cancer is the identification of the genes modulated by these oncoproteins, which permit cells to grow outside of their normal environment. Although it has been demonstrated that Slug is sufficient for generating leukemias and sarcomas, and for the growth of these cells to take place independently of expression of Slug itself, these results do not imply that the oncogenes associated with mesenchymal cancers need Slug for producing malignant transformation. BCR-ABL oncogenes [Sánchez-García & Grütz, PNAS (1995), 92:5287-5291] were used as a model for investigating this. BCR-ABL oncogenes activate the expression of Slug in Ba/F3 cells and in blastocytes derived from transgenic mice that express BCR-ABL (FIGS. 5A and 5B). Expression of Slug also occurs in blastocytes obtained from patients with Ph$^1$-positive human leukemias, whereas the product of the Slug gene was absent from the cells of normal human samples (FIG. 5C, lane 1). Conversely, Slug is present in t(9;22)-positive cell lines derived from patients with chronic myeloid leukemia (CML) and with acute lymphocytic leukemia (ALL), in cells of Ph$^1$-positive patients, and in other leukemic cell lines lacking t(9;22), including the B early 697 line, the myeloid U937, and the cell lines T ALL-SIL and KOPTI-KI (FIG. 5C). These and other earlier observations show that expression of Slug is a characteristic that is common in mesenchymal tumors.

Figure 6A:
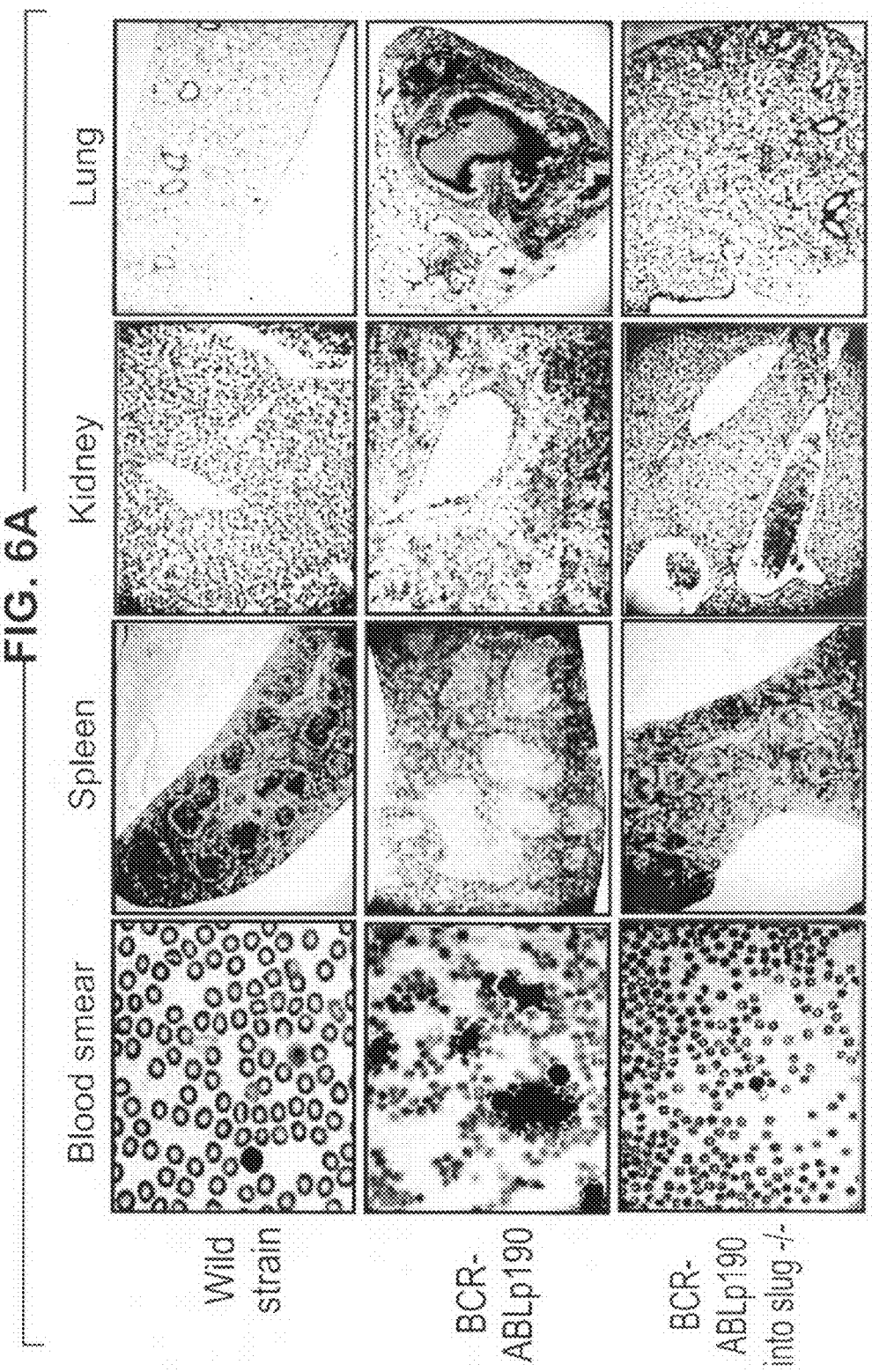
FIG. 6A shows the histological appearance of blood smears (Giemsa staining) and tissues (sections stained with hematoxylin/eosin).
Figure 6B:
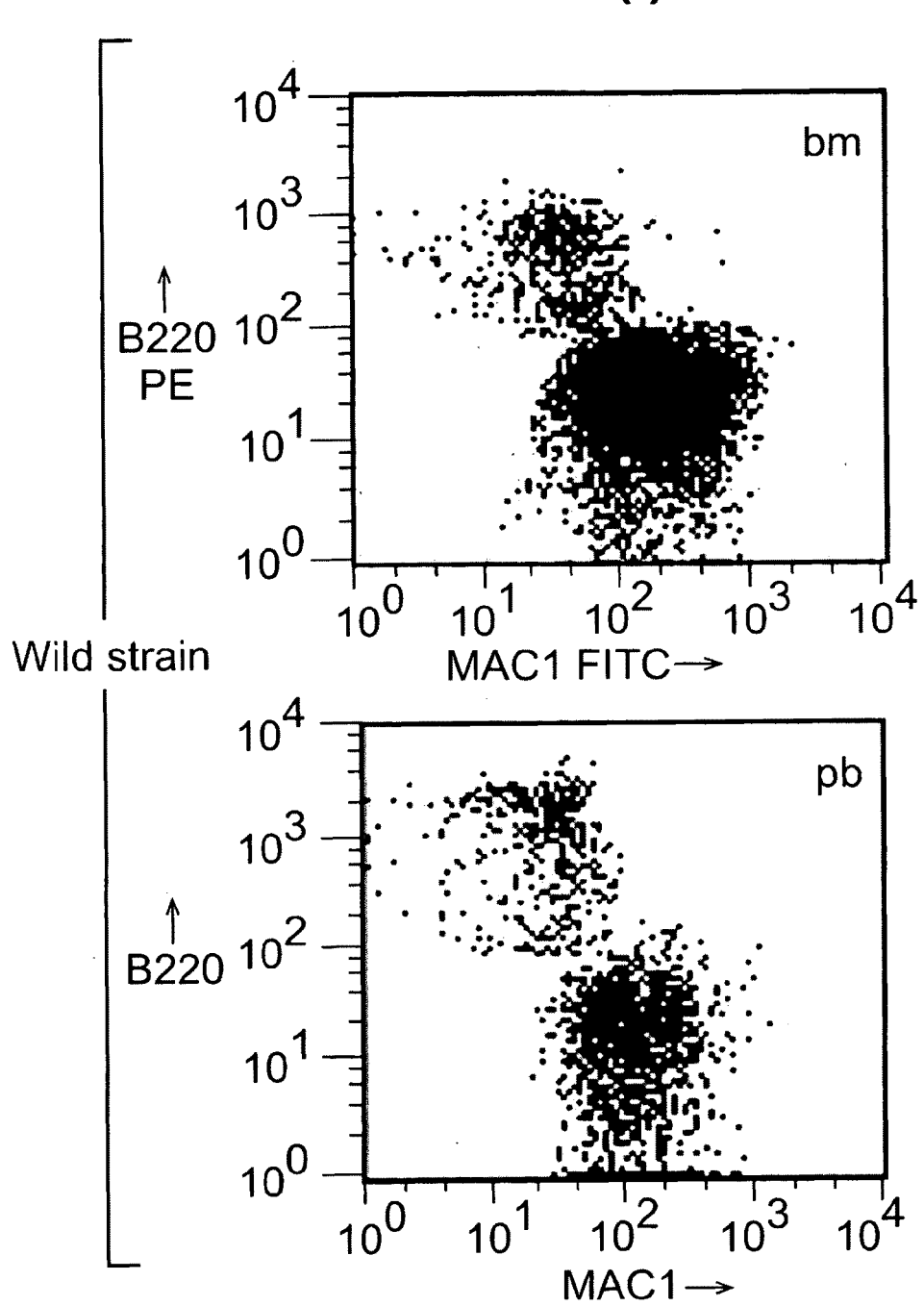
FIG. 6B shows the result of an analysis by flow cytometry of the bone marrow (bm) and of the blood (pb) with specific combinations of antibodies. Mice of the genotypes that are indicated were crossed and the genotype of the progeny was determined. It should be emphasized that the BCR-ABL$^{p190}$ mice had acute lymphoblastic leukemia (B-ALL), characteristic of the presence of blastocytes that coexpress Mac-1 and B220. This type of leukemia is also characterized by the infiltration of the spleen, liver and lungs, and by the presence of lymphoblastocytes in blood smears. However, the BCR-ABL$^{p190}$ mice did not develop leukemia in the absence of Slug (Slug −/−).

With the aim of demonstrating whether Slug is necessary for the genesis of leukemia induced by BCR-ABL, we investigated the leukemia-inducing capacity of BCR-ABL$^{p190}$ in the presence and absence of Slug. In humans, this oncogene is linked to leukemic B cells that coexpress myeloid markers. Next, BCR-ABL$^{p190}$ transgenic mice were generated. Histological and phenotypic examination of the BCR-ABL$^{p190}$ transgenic mice between 7 and 9 months of age confirmed the presence of blastocytes in hematopoietic and non-hematopoietic tissues (FIG. 6A). In a manner very similar to that which takes place in humans, these blastocytes coexpress myeloid and B-cell markers (FIG. 6B). Next, we undertook biological investigation of BCR-ABL$^{p190}$-B-ALL [transgenic mice with type B acute lymphoblastic leukemia (EP 1354962)] in the absence of Slug. Twelve BCR-ABL$^{p190}$ transgenic homozygotic mice, for the specific mutation of the Slug gene, were generated. Between 6 and 9 months of age, the blood of these BCR-ABL$^{p190}$×Slug −/− mice was analyzed periodically and no blastocytes were detected. The mice were sacrificed at 12 months of age, and autopsy showed that there were no significant morphological abnormalities of the hematopoietic and non-hematopoietic tissues. Despite extensive analysis, both histological and phenotypic, no sign of leukemia was observed in said BCR-ABL$^{p190}$×Slug −/− mice (FIG. 6). These results demonstrate that Slug plays a fundamental role in the genesis of BCR-ABL$^{p190}$ cancerous cells.

III. Discussion

The importance of Slug in each of the aspects of the phenotypes generated by the mice that express Slug has been investigated in detail. This investigation employed a system that contains, in a single plasmid, the elements of regulation and expression of the original binary system of tetracycline, which permits increased induction and great control of genetic expression by tetracycline in the mouse. In the mouse, Slug is not involved in the epithelial-mesenchymal transitions. In agreement with this idea, neither epithelial changes nor carcinomas were observed in any of the CombitTA-Slug transgenic mice analyzed. Analysis of all aspects of the human phenotypes related to the expression of Slug in mice that express Slug revealed that these mice had mesenchymal cancers, primarily leukemias.

In the hematopoietic system, the normal, uncompromised stem cells differentiate into mature cells. During this transition, expression of Slug is inactivated. In physiological situations, when these normal, uncompromised stem cells migrate, Slug favors their survival and permits them to perform their function. If this is not achieved within a certain time, these cells undergo apoptosis as a response to the absence of specific external signals. Therefore, the mesenchymal cancers that are observed in the CombitTA-Slug transgenic mice represent a demonstration in vivo of the idea that transformation depends on genetic changes that permit the undifferentiated cells to grow outside of their normal environment (FIG. 3). These results provide evidence that expression of Slug endows the cells with migratory capacity. In that case, Slug might become an attractive therapeutic target for controlling the invasive capacity of human cancers. However, although the survival conferred by Slug is reversible in vitro (FIG. 1), the changes induced by Slug are independent of its actual expression in vivo.

These findings also place the biological function of Slug in the context of cellular transformation dependent on BCR-ABL oncogenes. The data presented here demonstrate that the BCR-ABL oncogenes induce expression of Slug. In fact, expression of Slug is not rare in mesenchymal tumors (both leukemias and sarcomas), in which the transformation has been produced by other genetic changes. This suggests that Slug might be involved in tumoral invasion, not only in BCR-ABL-positive leukemias, but also, possibly, in other mesenchymal cancers.

With the aim of demonstrating whether Slug is necessary for the genesis of leukemia induced by BCR-ABL, the leukemia-inducing capacity of the BCR-ABL$^{p190}$ oncogene was investigated in the presence and absence of Slug. The results obtained demonstrate that Slug has a fundamental role in the biology of BCR-ABL cancers. These data are consistent with a model in which tumor cells that contain the BCR-ABL fusion protein express Slug constitutively, which promotes the aberrant survival and migration of the defective cells in various environments (FIG. 3). Since Slug is frequently found in cells of mesenchymal tumors, it is possible that Slug has a more general role in the biology of cancer than that specifically associated with transformation by BCR-ABL. Thus, expression of Slug might constitute a route of invasion common to leukemias and sarcomas associated with other proteins.

In conclusion, Slug might represent a mechanism of tumoral invasion widely distributed in mesenchymal tumors. Thus, Slug might be an attractive therapeutic target for controlling tumoral invasive capacity, and can be regarded as a marker of malignancy.

Example 2

Expression of the Slug Gene as a Marker of the Early Spread of Cancer

I. Material and Methods

Selection of Patients 124 patients with a diagnosis of breast carcinoma were selected (81 patients with metastasized breast cancer and 43 patients with stage TNM0 breast cancer), from whom 10 ml of blood was taken before they were administered the first cycle of chemotherapy and the same amount before they received the last cycle. At the end of the treatment with adjunctive chemotherapy, the patients were monitored every 3 months during the first 2 years, and every 6 months during the following 3 years, i.e. for a total of 5 years.

Analysis of Slug Expression

The methodology employed for determination of expression of the Slug gene in blood was:
- Extraction of RNA from peripheral blood using the QIAamp® kit following the manufacturer's instructions
- Removal of contaminating DNA by treating the samples with DNAse I following the manufacturer's instructions
- Obtaining cDNA from the RNA treated with DNAse using the Promega® kit following the manufacturer's instructions
- The integrity of the cDNA was verified by amplification of the actin with the appropriate oligos:

```
Actin-F:                                      (SEQ ID NO: 8)
5'-TAG GAA TCC ATG GCC ACT GCC GCA TCC TCT TCC-3'

Actin-B:                                      (SEQ ID NO: 9)
5' - CAC GAT GGA GGG GCC GGA CTC ATC - 3'
```

- 35 cycles at 95° C. for 1 minute/55° C. for 1 minute/72° C. for 1 minute and 30 seconds
- RT-PCR for detecting expression of the Slug gene. Oligos with the following characteristics were used:

```
                                              (SEQ ID NO: 10)
hSlug-F:   5'-AGC GAA CTG GAC ACA CAT A-3'

(SEQ ID NO: 11)
hSlug-B:   5'-AAT GCT CTG TTG CAG TGA G-3'
```

- 35 cycles at 95° C. for 1 minute/55° C. for 1 minute/72° C. for 1 minute and 30 seconds
- Electrophoresis in 1% agarose gel, at 55 V for 1 hour, to see the result of RT-PCR [García-Hernández et al., (1997) PNAS, 94:13239-13244]
- Transfer to nylon membranes and hybridization with Slug probe [García-Hernández et al., (1997) PNAS, 94:13239-13244]

II. Results

Figure 7:
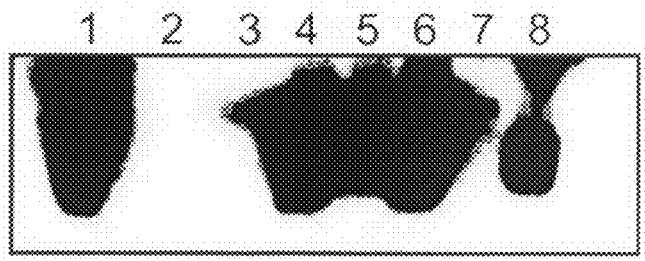
FIG. 7 shows the result of analysis of the expression of hSlug in cell lines and tissues of breast cancer. Expression of Slug was analyzed by RT-PCR. Lane 1: positive control (human line that expresses Slug, K562); lane 3: control without cDNA; lanes 4-7: primary tissues of breast cancer; lane 8: MCF-7 cell line.

Initially, expression of Slug in cell lines and tumoral tissues of breast cancer was investigated. As shown in FIG. 7, both the MCF-7 cell line (FIG. 7, lane 8) derived from a breast adenocarcinoma, and the primary breast carcinomas (FIG. 7, lanes 4-7), express Slug.

Figure 8:
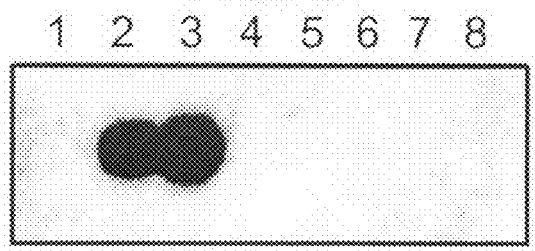
FIG. 8 shows the result of analysis of the expression of hSlug in the blood of healthy (human) individuals. Lane 1: control without cDNA; lanes 2-3: blood from individuals with breast cancer as positive control; lanes 4-8: blood from healthy individuals.
Figure 9:
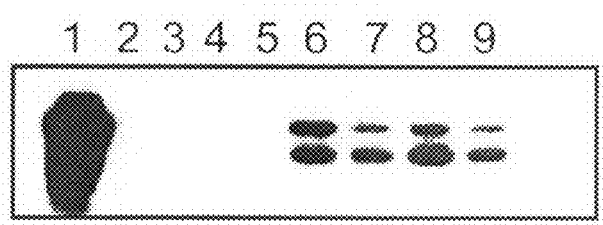
FIG. 9 shows the result of analysis of the expression of hSlug in the blood of (human) individuals with metastasized breast cancer. Expression of hSlug was analyzed by RT-PCR. Lane 1: K562 cell line as positive control; lane 3: control without cDNA; lanes 4-9: patients with metastasized breast cancer.

After confirming the presence of Slug in breast cancers, an investigation of the expression of Slug in the blood of patients with breast cancer was undertaken. As shown in FIG. 8, Slug is not expressed in the blood of healthy individuals; however, expression of Slug was detected in 58% of the cases of metastasized breast cancer targeted with variable chemotherapy treatments (FIG. 9).

Figure 10:
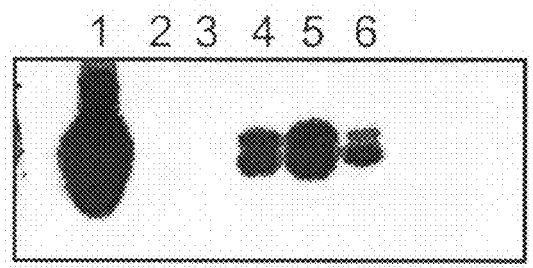
FIG. 10 shows the result of analysis of the expression of hSlug in (human) patients with breast cancer in stage TNM0. Expression of hSlug was analyzed by RT-PCR. Lane 1: K562 as positive control; lane 3: control without cDNA; lane 4: metastasized breast cancer; lanes 5-6: stage TNM0 breast cancer.

Once the expression of Slug had been detected in a clear majority of metastasized breast cancers, a study of patients diagnosed with stage TNM0 breast cancer was undertaken. As shown in FIG. 10, the presence of Slug was detected in 65% of the patients with stage TNM0 breast cancer.

III. Discussion

The results obtained indicate that Slug can serve as a marker of early spread of breast cancer and of other types of cancer, both epithelial and mesenchymal. Therefore, investigation of the expression of Slug in blood can be used for monitoring diagnosis, therapeutic benefit and relapse in cancer patients.

The invention claimed is:

1. An in-vitro method for evaluating a predisposition of a human subject with epithelial cancer and/or breast cancer to develop metastasis which comprises:
   (a) detecting, identifying and/or quantifying transcription of the Slug gene, in a sample of blood, or a derivative thereof, from said human subject, and
   (b) evaluating the predisposition of the human subject to develop metastasis, wherein the presence of transcription products of the Slug gene in the blood or derivative thereof indicates the predisposition of said human subject to develop metastasis.

2. The method as claimed in claim 1, characterized in that said detecting, identifying and/or quantifying is of a product of transcription selected from messenger RNA (mRNA) of the Slug gene, a fragment of said mRNA, complementary DNA (cDNA) to the RNA that encodes the product of transcription or expression of said Slug gene, a fragment of said cDNA, and mixtures thereof.

3. The method as claimed in claim 1, characterized in that said human subject has a cancer whose cancerous cells are Slug+.

4. The method as claimed in claim 1, characterized in that said epithelial and/or breast cancer is selected from the group consisting of epithelial lung cancer, epithelial gynecological tumors, epithelial ovarian cancer, breast carcinoma, or epithelial colon cancer.

5. The method as claimed in claim 3, characterized in that said epithelial and/or breast cancer is selected from the group consisting of epithelial lung cancer, epithelial gynecological tumors, epithelial ovarian cancer, breast carcinoma, or epithelial colon cancer.

* * * * *

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Artificial sequence
<220> FEATURE:
<221> NAME/KEY: Synthetic DNA
<223> OTHER INFORMATION: Oligonucleotide designed for analyzing the
      expression of CombitTA-Slug

<400> SEQUENCE: 1
ttgagtgcat tctagttgtg                                              20
```

<210> SEQ ID NO 2
<211> LENGTH: 21
<212> TYPE: DNA
<213> ORGANISM: Artificial Sequence
<220> FEATURE:
<223> OTHER INFORMATION: Artificial sequence
<220> FEATURE:
<221> NAME/KEY: Synthetic DNA
<223> OTHER INFORMATION: Direct oligonucleotide designed for analyzing
      the expression of mSlug

<400> SEQUENCE: 2
gtttcagtgc aatttatgca a                                          21

<210> SEQ ID NO 3
<211> LENGTH: 20
<212> TYPE: DNA
<213> ORGANISM: Artificial Sequence
<220> FEATURE:
<223> OTHER INFORMATION: Artificial sequence
<220> FEATURE:
<221> NAME/KEY: Synthetic DNA
<223> OTHER INFORMATION: Reverse oligonucleotide designed for analyzing
      the expression of mSlug

<400> SEQUENCE: 3
ttatacatac tatttggttg                                            20

<210> SEQ ID NO 4
<211> LENGTH: 20
<212> TYPE: DNA
<213> ORGANISM: Artificial Sequence
<220> FEATURE:
<223> OTHER INFORMATION: Artificial sequence
<220> FEATURE:
<221> NAME/KEY: Synthetic DNA
<223> OTHER INFORMATION: Direct oligonucleotide designed for analyzing
      the expression of hSlug in human cell lines and blood samples from
      Ph1-positive patients

<400> SEQUENCE: 4
gcctccaaaa agccaaacta                                            20

<210> SEQ ID NO 5
<211> LENGTH: 20
<212> TYPE: DNA
<213> ORGANISM: Artificial Sequence
<220> FEATURE:
<223> OTHER INFORMATION: Artificial sequence
<220> FEATURE:
<221> NAME/KEY: Synthetic DNA
<223> OTHER INFORMATION: Reverse oligonucleotide designed for analyzing
      the expression of hSlug in human cell lines and blood samples from
      Ph1-positive patients

<400> SEQUENCE: 5
cacagtgatg gggctgtatg                                            20

<210> SEQ ID NO 6
<211> LENGTH: 20
<212> TYPE: DNA
<213> ORGANISM: Artificial Sequence
<220> FEATURE:
<223> OTHER INFORMATION: Artificial sequence
<220> FEATURE:
<221> NAME/KEY: Synthetic DNA
<223> OTHER INFORMATION: Direct oligonucleotide designed for analyzing
      the expression of c-ABL

<400> SEQUENCE: 6
gtatcatctg actttgagcc                                          20

<210> SEQ ID NO 7
<211> LENGTH: 20
<212> TYPE: DNA
<213> ORGANISM: Artificial Sequence
<220> FEATURE:
<223> OTHER INFORMATION: Artificial sequence
<220> FEATURE:
<221> NAME/KEY: Synthetic DNA
<223> OTHER INFORMATION: Reverse oligonucleotide designed for analyzing
      the expression of c-ABL

<400> SEQUENCE: 7
gtaccaggag tgtttctcca                                          20

<210> SEQ ID NO 8
<211> LENGTH: 33
<212> TYPE: DNA
<213> ORGANISM: Artificial Sequence
<220> FEATURE:
<223> OTHER INFORMATION: Artificial sequence
<220> FEATURE:
<221> NAME/KEY: Synthetic DNA
<223> OTHER INFORMATION: Direct oligonucleotide designed for analyzing
      the expression of actin

<400> SEQUENCE: 8
taggaatcca tggccactgc cgcatcctct tcc                           33

<210> SEQ ID NO 9
<211> LENGTH: 24
<212> TYPE: DNA
<213> ORGANISM: Artificial Sequence
<220> FEATURE:
<223> OTHER INFORMATION: Artificial sequence
<220> FEATURE:
<221> NAME/KEY: Synthetic DNA
<223> OTHER INFORMATION: Reverse oligonucleotide designed for analyzing
      the expression of actin

<400> SEQUENCE: 9
cacgatggag gggccggact catc                                     24

<210> SEQ ID NO 10
<211> LENGTH: 19
<212> TYPE: DNA
<213> ORGANISM: Artificial Sequence
<220> FEATURE:
<223> OTHER INFORMATION: Artificial sequence
<220> FEATURE:
<221> NAME/KEY: Synthetic DNA
<223> OTHER INFORMATION: Direct oligonucleotide designed for analyzing
      the expression of the Slug gene

<400> SEQUENCE: 10
agcgaactgg acacacata                                           19

<210> SEQ ID NO 11
<211> LENGTH: 19
<212> TYPE: DNA
<213> ORGANISM: Artificial Sequence
<220> FEATURE:
<223> OTHER INFORMATION: Artificial sequence
<220> FEATURE:

```
-continued

<221> NAME/KEY: Synthetic DNA
<223> OTHER INFORMATION: Reverse oligonucleotide designed for analyzing
      the expression of the Slug gene

<400> SEQUENCE: 11
aatgctctgt tgcagtgag                                                    19
```